(12) United States Patent
Charlton

(10) Patent No.: US 6,485,982 B1
(45) Date of Patent: Nov. 26, 2002

(54) TEST DEVICE AND METHOD FOR COLORED PARTICLE IMMUNOASSAY

(75) Inventor: David E. Charlton, Allentown, NJ (US)

(73) Assignee: Armkel, LLC, Princeton, NJ (US)

( * ) Notice: Subject to any disclaimer, the term of this patent is extended or adjusted under 35 U.S.C. 154(b) by 0 days.

(21) Appl. No.: 08/465,675

(22) Filed: Jun. 6, 1995

Related U.S. Application Data

(63) Continuation of application No. 07/995,331, filed on Dec. 23, 1992, now Pat. No. 5,714,389, which is a continuation of application No. 07/702,450, filed on May 16, 1991, now abandoned, which is a continuation of application No. 07/211,582, filed on Jun. 27, 1988, now abandoned.

(51) Int. Cl.[7] .............................................. G01N 33/558

(52) U.S. Cl. ........................ 436/514; 422/55; 422/56; 422/57; 427/2.11; 435/176; 435/7.92; 435/970; 436/169; 436/178; 436/518; 436/523; 436/524; 436/525; 436/533; 436/544; 436/810; 436/814; 436/817; 436/818

(58) Field of Search ..................... 422/55–57; 427/2.11; 435/176, 7.92, 970; 436/514, 518, 523, 524, 525, 533, 544, 169, 178, 810, 814, 817, 818

(56) References Cited

U.S. PATENT DOCUMENTS

| 3,620,677 A | 11/1971 | Morison ........................ 23/253 |
| 3,811,840 A | 5/1974 | Bauer et al. ............. 23/253 TP |
| 3,888,629 A | 6/1975 | Bagshawe ................. 23/230 B |

(List continued on next page.)

FOREIGN PATENT DOCUMENTS

| AU | A 63502/86 | 10/1986 |
| DE | 3044385 | 6/1982 |
| DE | 3432083 | 3/1986 |

(List continued on next page.)

OTHER PUBLICATIONS

Greenquist et al., "Homogenous Fluorescent Immunoassay with Dry Re–agents," Clinical Chemistry, vol. 27, No. 9, 1981 pp. 1614–1617.

Collins, H.W.P., "Alternative Immunoassays", Ed. John Wiley & Sons, 1985 pp. 34–57.

Surek, B. "Visualization of Antigenic Proteins Blotted onto Nitrocellulose Using The Immuno–Gold Staining (IGS) Method" Biochemical and Biophysical Research Communications, 121 (1), 284–289, 1984.

Hsu, Y.–H. , "Immunogold for Detection of Antigen on Nitrocellulose Paper" Anal. Biochem., 142, 221–225, 1984.

Puissieux, F et al., "Les Liposomes; Applications Therapeutiques" Technique et Documentation (Lavoisier) 1985, Ch. 2, p. 48 (French, with translation).

(List continued on next page.)

Primary Examiner—Christopher L. Chin
(74) Attorney, Agent, or Firm—Testa Hurwitz & Thibeault LLP

(57) ABSTRACT

Disclosed is a test cell and a method for detection of a preselected ligand in a liquid sample such as a body fluid. The test cell includes an elongate outer casing which houses an interior permeable material capable of transporting an aqueous solution and defining a sample inlet, a test volume, and a reservoir volume. The reservoir volume is disposed in a section of the test cell spaced apart from the inlet and is filled with sorbent material. The reservoir acts to receive liquid transported along a flow path defined by the permeable material and extending from the inlet and through the test volume. In the test volume is a test site which includes a first protein having a binding site specific to a first epitope of the ligand immobilized in fluid communication with the flow path. The test site can be observed through a window of the casing.

38 Claims, 2 Drawing Sheets

U.S. PATENT DOCUMENTS

| | | | | |
|---|---|---|---|---|
| 4,042,335 | A | 8/1977 | Clement | 23/253 |
| 4,045,384 | A | 8/1977 | Dorman | 260/8 |
| 4,094,647 | A | 6/1978 | Deutsch et al. | 23/253 |
| 4,168,146 | A | 9/1979 | Grubb et al. | 23/230 |
| 4,169,138 | A | 9/1979 | Jonsson | 424/12 |
| RE30,267 | E | 5/1980 | Bruschi | |
| 4,205,952 | A | 6/1980 | Cais | 23/230 B |
| 4,219,335 | A | 8/1980 | Ebersole | 23/230 B |
| 4,235,601 | A | 11/1980 | Deutsch et al. | 23/230 |
| 4,256,834 | A | 3/1981 | Zuk et al. | 435/7 |
| 4,258,001 | A | 3/1981 | Pierce et al. | 422/56 |
| 4,294,818 | A | 10/1981 | McMichael et al. | 424/12 |
| 4,297,344 | A | 10/1981 | Schwinn et al. | |
| 4,313,734 | A | 2/1982 | Leuvering | 23/230 |
| 4,348,207 | A | 9/1982 | Cappel | 23/230 B |
| 4,357,142 | A | 11/1982 | Schall, Jr. et al. | 23/230 B |
| 4,361,537 | A | 11/1982 | Deutsch et al. | 422/56 |
| 4,366,241 | A | 12/1982 | Tom et al. | 435/7 |
| 4,373,932 | A | 2/1983 | Gribnau et al. | 436/501 |
| 4,376,110 | A | 3/1983 | David et al. | 436/513 |
| 4,411,518 | A | 10/1983 | Meserol et al. | 356/39 |
| 4,419,453 | A | 12/1983 | Dorman et al. | 436/534 |
| 4,434,150 | A | 2/1984 | Azad et al. | 424/1.1 |
| 4,435,504 | A | 3/1984 | Zuk et al. | 435/7 |
| 4,446,232 | A | 5/1984 | Liotta | 435/7 |
| 4,459,358 | A | 7/1984 | Berke | 436/170 |
| 4,477,575 | A | 10/1984 | Vogel et al. | 436/170 |
| 4,486,530 | A | 12/1984 | David et al. | 435/7 |
| 4,487,839 | A | 12/1984 | Kamentsky | 436/518 |
| 4,496,654 | A | 1/1985 | Katz et al. | 435/7 |
| 4,503,143 | A | 3/1985 | Gerber et al. | 435/7 |
| 4,508,829 | A | 4/1985 | Sulitzeanu | 436/510 |
| 4,515,889 | A | 5/1985 | Klose et al. | 435/4 |
| 4,537,861 | A | 8/1985 | Elings et al. | 436/518 |
| 4,552,839 | A | 11/1985 | Gould et al. | 435/7.9 |
| 4,590,169 | A | 5/1986 | Cragle et al. | 436/523 |
| 4,594,327 | A | 6/1986 | Zuk | 436/514 |
| 4,604,364 | A | 8/1986 | Kosak | 436/501 |
| 4,623,461 | A | 11/1986 | Hossom et al. | 210/445 |
| 4,624,929 | A | 11/1986 | Ullman | 436/179 |
| 4,632,901 | A | 12/1986 | Valkirs et al. | 435/5 |
| 4,639,242 | A | 1/1987 | Babson | 494/37 |
| 4,639,419 | A | 1/1987 | Olson et al. | 435/5 |
| 4,647,544 | A | 3/1987 | Nicoli et al. | 436/518 |
| 4,654,309 | A | 3/1987 | Milnar et al. | 922/56 |
| 4,665,034 | A | 5/1987 | Chandler | 435/287 |
| 4,666,863 | A | 5/1987 | Edwards et al. | |
| 4,690,907 | A | 9/1987 | Hibino et al. | 436/514 |
| 4,703,017 | A | 10/1987 | Campbell et al. | 436/518 |
| 4,740,468 | A | 4/1988 | Weng et al. | |
| 4,756,828 | A | 7/1988 | Litman et al. | 435/7.9 |
| 4,757,004 | A | 7/1988 | Houts et al. | 435/7.9 |
| 4,761,381 | A | 8/1988 | Blatt et al. | 436/165 |
| 4,770,853 | A | 9/1988 | Bernstein | 422/58 |
| 4,772,550 | A | 9/1988 | Greenquist | 435/7.9 |
| 4,774,192 | A | 9/1988 | Terminiello et al. | 436/540 |
| 4,366,241 | A | 10/1988 | Tom et al. | 435/7 |
| 4,778,751 | A | 10/1988 | El Shami et al. | 435/7.9 |
| 4,803,170 | A | 2/1989 | Stanton et al. | 436/518 |
| 4,806,311 | A | 2/1989 | Greenquist | 422/56 |
| 4,806,312 | A | 2/1989 | Greenquist | 422/56 |
| 4,853,335 | A | 8/1989 | Olsen et al. | 436/527 |
| 4,857,453 | A | 8/1989 | Ullman et al. | 435/7 |
| 4,859,612 | A | 8/1989 | Cole et al. | 436/523 |
| 4,861,711 | A | 8/1989 | Friesen et al. | 436/7 |
| 4,868,108 | A | 9/1989 | Bahar et al. | 435/7.9 |
| 4,879,215 | A | 11/1989 | Weng et al. | |
| 4,883,688 | A | 11/1989 | Houts et al. | 427/285 |
| 4,891,313 | A | 1/1990 | Berger et al. | 436/7 |
| 4,916,056 | A | 4/1990 | Brown, III et al. | 435/7 |
| 4,920,046 | A | * 4/1990 | McFarland et al. | 435/7 |
| 4,945,042 | A | 7/1990 | Geiger et al. | 435/7 |
| 4,954,452 | A | 9/1990 | Yost et al. | |
| 4,956,302 | A | 9/1990 | Gordon et al. | 436/161 |
| 4,959,307 | A | 9/1990 | Olson | |
| 4,960,691 | A | 10/1990 | Gordon et al. | 435/6 |
| 4,962,023 | A | 10/1990 | Todd et al. | 435/7 |
| 4,963,468 | A | 10/1990 | Olson | 435/7 |
| 4,981,785 | A | 1/1991 | Nayak | 435/7 |
| 4,981,786 | A | 1/1991 | Dafforn et al. | 435/7 |
| 4,985,204 | A | 1/1991 | Klose et al. | 422/56 |
| 4,999,285 | A | 3/1991 | Stiso | 435/7.9 |
| 5,006,474 | A | 4/1991 | Horstman et al. | 422/56 |
| 5,008,080 | A | 4/1991 | Brown, III et al. | 422/56 |
| 5,030,558 | A | 7/1991 | Litman et al. | 435/7.91 |
| 5,039,607 | A | 8/1991 | Skold et al. | 435/7.5 |
| 5,043,428 | A | 8/1991 | Heimburger et al. | |
| 5,073,484 | A | 12/1991 | Swanson et al. | |
| 5,075,078 | A | 12/1991 | Osikowicz et al. | |
| 5,085,987 | A | 2/1992 | Olson | |
| 5,085,988 | A | 2/1992 | Olson | |
| 5,120,504 | A | 6/1992 | Petro-Roy et al. | 422/58 |
| 5,120,643 | A | 6/1992 | Ching et al. | 435/7.92 |
| 5,141,850 | A | 8/1992 | Cole et al. | 436/525 |
| 5,141,875 | A | 8/1992 | Kelton et al. | 436/514 |
| 5,149,622 | A | * 9/1992 | Brown et al. | 435/5 |
| 5,156,952 | A | 10/1992 | Litman et al. | 435/7.91 |
| 5,160,701 | A | 11/1992 | Brown, III et al. | |
| 5,164,294 | A | 11/1992 | Skold et al. | 435/7.5 |
| 5,232,835 | A | 8/1993 | Litman et al. | 435/7.93 |
| 5,248,619 | A | 9/1993 | Skold et al. | 436/514 |
| RE34,405 | E | 10/1993 | Gould et al. | |
| 5,254,458 | A | 10/1993 | Mimms | |
| 5,260,193 | A | 11/1993 | Olson | |
| 5,260,194 | A | 11/1993 | Olson | |
| 5,459,078 | A | 10/1995 | Kline et al. | |
| 5,459,080 | A | 10/1995 | Adamczyck et al. | |
| 5,541,115 | A | 7/1996 | Siegel et al. | |
| 5,591,645 | A | 1/1997 | Rosenstein | 436/514 |
| 5,602,040 | A | 2/1997 | May et al. | 436/514 |
| 5,622,871 | A | 4/1997 | May et al. | 436/514 |
| 5,654,162 | A | 8/1997 | Guire et al. | |
| 5,656,503 | A | 8/1997 | May et al. | 436/514 |
| 5,670,381 | A | 9/1997 | Jou et al. | |
| 5,686,315 | A | 11/1997 | Pronovost et al. | 436/510 |
| 5,710,005 | A | 1/1998 | Rittenberg | |
| 5,714,389 | A | 2/1998 | Charlton et al. | |
| 5,716,778 | A | 2/1998 | Weng et al. | |
| 5,866,322 | A | 2/1999 | Jou et al. | |
| 5,895,750 | A | 4/1999 | Mushahwar et al. | |
| 5,989,921 | A | 11/1999 | Charlton et al. | |
| 6,020,147 | A | 2/2000 | Guire et al. | |

FOREIGN PATENT DOCUMENTS

| | | |
|---|---|---|
| DE | 8 805 565 | 9/1988 |
| EP | 0007654 | 2/1980 |
| EP | 0018561 | 4/1980 |
| EP | 0032270 | 7/1981 |
| EP | 0063810 | 11/1982 |
| EP | 0088636 | 9/1983 |
| EP | 0149168 A1 | 7/1985 |
| EP | 0154749 A1 | 9/1985 |
| EP | 0158746 | 10/1985 |
| EP | 0164180 | 12/1985 |
| EP | 0 170 746 A1 | 2/1986 |
| EP | 0183442 A2 | 6/1986 |
| EP | 0186799 | 7/1986 |
| EP | 0 191 640 A2 | 8/1986 |
| EP | 192 320 | 8/1986 |
| EP | 0201079 | 11/1986 |
| EP | 0212603 A2 | 3/1987 |

| EP | 0 217 403 A2 | 4/1987 |
| --- | --- | --- |
| EP | 0 225 054 A1 | 6/1987 |
| EP | 0 250 137 A2 | 12/1987 |
| EP | 0 258 963 A2 | 3/1988 |
| EP | 0271204 A2 | 6/1988 |
| EP | 0284232 A1 | 9/1988 |
| EP | 0291194 | 11/1988 |
| EP | 0299428 A2 | 1/1989 |
| EP | 0306336 | 3/1989 |
| EP | 0337082 | 10/1989 |
| EP | 0349215 | 1/1990 |
| EP | 0320240 | 3/1991 |
| EP | 0420021 A2 | 4/1991 |
| EP | 212599 B1 | 10/1991 |
| EP | 0505636 A1 | 9/1992 |
| EP | 0560410 | 9/1993 |
| EP | 0560411 | 9/1993 |
| EP | 0284232 | 6/1995 |
| FR | 2356944 | 1/1978 |
| GB | 2 016 687 A | 9/1979 |
| GB | 2204398 | 11/1988 |
| NL | 8703007 | 1/1989 |
| WO | WO 86/03839 | 7/1986 |
| WO | WO 86/04683 | 8/1986 ............... 435/7.9 |
| WO | WO 87/02774 | 5/1987 ............... 435/7.9 |
| WO | WO 88/05912 | 8/1988 |
| WO | WO88/08534 | 11/1988 |
| WO | WO 91/12528 | 8/1991 |

OTHER PUBLICATIONS

Syva, Syntex Company, Product Brochure "Acculevel; Acculevel TDM Assays", pp. 1–6, Sep. 1987.

Frens, "Controlled Nucleation for the Regulation of the Particle Size in Monodisperse Gold Suspensions," *241 Nature Physical Science* 20–22 (1973).

Horisberger, "Evaluation of Colloidal Gold as a Cytochromic Marker for Transmission and Scanning Electron Microscopy," 36 Biol. Cellulaire 253–58 (1979).

Leuvering, et al, "Sol Particle Immunoassay (SPIA)," 1 (1) J. Immunoassay 77–91 (1980).

Tijssen, Laboratory Techniques in Biochemistry and Molecular Biology, vol. 15, "Practice and Theory of Enzyme Immunoassays," Chapter 13—The Immobilization of Immunoreactants on Solid Phases, 297–328.

Lou, et al., One–Step Competitive Immunochromatographic Assay for Semiquantitative Determination of Lipoprotein(a) in Plasma, 39(4) Clin. Chem 619–624 (1993).

Gribnau, et al., Particle–Labelled Immunoassays: A Review, 376 J. of Chromatography Biomedical Applications 175–189 (1986).

Leuvering, et al., Optimization of a Sandwich Sol Particle Immunoasay for Human Chorionic Gonadotrophin, 62 J. Of Immunological Methods 175–184 (1983).

Fichter, Ueber die kapillarelektrische Fällung positiver Kolloide Zeitschrift Für Chemie Und Industrie Der Kolliode 1–2 (1911). No English translation.

J. Perrin, Mécanisme de L'Electrisation de Contact et Solutions Colloidales, Tome III J. De Chimie Physique 50–160 (1905). No English translation.

J. Perrin, Mécanisme de L'Electrisation de Contact et Solutions Colloidales, Tome III J. De Chimie Physique 601–51 (1904). No English translation.

Fichter, et al., Die Kapillaranalyse Kolloidaler Lösungen, 21 Verhandl Naturforsch.Ges.Basel 2–24 (1910). No English translation.

Runge, Die Runft der Farbenbereitung, Farbenchemie (1980). 1–288 No English translation.

Lederer, M., "Chromatographic Properties of Two Gold Compounds Used in the Therapy of Polyarthritis", 153 Journal of Chromatography, 302–304 (1978).

Colloidal Metal Marking Reference Book (1984–85), vol. 2, No. 1, pp. 1–44.

H. Weil, The Evolution of Paper Chromatography, 132 Kolloid–Z (1953), pp. 149–162.

H. Weil, Der Ursprung der Papierchromatographie, 40 Naturwissenschaften (1953), pp. 1–7 No English Translation.

Sahlbom, V.N., "Kapilaranalyse Kolloider Lösungen", 2 Kolloidchemische Beihefte, Band II, Heft 3–4, pp. 79–140, Verlag Von Theodor Steinkopff, Dresden–A (1910–11). No English translation.

E. Blasius and M. Fischer, Papierchromatographische und papierionophoretische Trennung der Platinelemente und des Goldes, 177 Z. Anal. Chem. (1960), pp. 412–420 No English translation.

E. Blasius and M. Fischer, Papierchromatographische und papierionophoretische Trennung der Elemente der Reduktiongruppe, 178 Z. Anal. Chem. (1960). pp. 28–33 No English translation.

F. Goppelstroder, Verhandl 3 Naturforsch. Ges. Basel 268 (1861).

Zuk, R.F., et al., Enzyme Immunochromatography—A Quantitative Immunoassay Requiring No Instrumentation, Clinical Chemistry, vol. 31, No. 7, pp. 1145–1150 (1985).

Bosch, A.M. G., "Enzym–und Sol Particle Immunoassays für Hormone", Gynecology and Obstetrics, pp. 509–512; 1987. English summary 1 page.

Moeremans, M., et al., "Sensitive Visualization of Antigen–Assays with Immunogold and Immunogold/Silver Staining", J. Immunological Methods, 74, pp. 353–360, 1984.

Maguire T.A., "Pregnancy and Ovulation Testing"; The Pharmaceutical Journal , 531–533, (1989), May 6.

Chard, T., "Pregnancy Tests: A Review", Human Reproduction, vol. 7, No. 5, pp. 701–710, 1952.

Brdicka, R., "Grundlagen Der Physikalischen Chemie", Ch. X. pp. 774–787; Veb Deutscher Verlag Der Wissenschaften, Berlin (1958). English summary 1 page.

Bredig–Leipzig, "Einige Anwendungen Des Elektnschen Lichtbogens", Zietschrist Für Electrochemie, Heft. 22, pp. 514–515; (1898). English summary 1 page.

Wiberg, E., "Lehrbuch Der Anorganischen Chemie", pp. 333–338, Walter De Gruyte & Co., Berlin, 1960. 1 page English Summary.

Unanue, E.R., Benacerraf, B.; "Immunfluoreszenz"; Immunologie, pp. 63–65; Walter de Gruyter, Berlin–New York 1987. English Translation.

Wright, J.F.; "A Simple Immunodiagnostic Test System for Alternate Site Market"; World Biotech Report, pp. 263–271; 1988.

Zsigmondy, R.; "Ueber Wassrige Lösungen Metallischer Goldes", Annalen Der Chemie, 301, pp. 29–54; 1898. English Translation by Morgan C. Larkin.

Van Hell, H., et al., "Particle Immunoassays"; Alternative Immunoassays, Ch. 4, pp. 40–59; 1985.

Collins, W.P.; "Expert Report"; In the High Court of Justice, Chancery Division, Patent Court; *Unilever PLC v. Chefaro Proprietaries Ltd.*, 1994.

Collins, W.P.' Statutory Declaration, In the matter of European Patent Application No. 88303744.2–2116 in the name of Unilever NV, 1992.

Stanley, C.J., "Affidavit", In the Matter of European Patent No. 291,194 to Unilever, NV and In the Matter of Opposition Thereto, 1994.

Stanley, C.J., "Witness Statement", In the High Court of Justice, Chancery Division, Patent Court *Unilever PLC v. Chefaro Proprietaries Ltd.,* 1994.

Verheijden, P., "Witness Statement", In the High Court of Justice, Chancery Division, Patent Court, *Unilever PLC v. Chefaro Proprietaries Ltd.,* 1994.

Collins, W.P., "Statutory Declaration No. 2", In the Matter of European Patent Application No. 88303744.2/291,194, In the Name of Unilever NV and Oppositions Thereto, 1995.

Giles, A.B., "Witness Statement", In the High Court of Justice, Chancery Division, Patent, Court, *Unilever PLC v. Chefaro Proprietaries Ltd.;* CH 1993. U. No. 3034; 1994.

Kronick, M.N., "Immunoassay Techniques with Fluorescent Phycobiliprotein Conjugates", Clinical Chemistry, 29/9, 1582–1586, 1983.

Baker, T.S., "Letter to Crawford G.L.: Clarification of Dual Analyte Protocols". 1983.

May, K., "Witness Statement", In the High Court of Justice, Chancery Division, Patent Court, *Unilever PLC v. Chefaro Proprietaries Ltd.;* 1993.

Welch, P.G., "Witness Statement", In the High Court of Justice, Chancery Division, Patent Court; *Unilever PLC v. Chefaro Proprietaries Ltd.;* 1994.

"Polar Bear Hits Town; OPUS Immunoassay System", *Diagnostic News,* issue 1, Mar. 1992, Behring. pp. 73–75.

"Summary of Pregslide 00 see Test Specifications", XII World Congress on Fertility & Sterility, Singapore, 1986.

Stanley, C.J., et al., "Enzyme Amplification Can Enhance Both the Speed and the Sensitivity of Immunoassays", J. Immunological Methods, 83, 89–95 (1985).

Stanley, C.J., et al., "Enzyme Amplification: A New Technique for Enhancing the Speed and Sensitivity of Enzyme Immunoassays", I.C.P.R., 44–51; Jul./Aug. 1985.

Johannsson, A., et al., "A Fast Highly Sensitive Colorimetric Enzyme Immunoassay System Demonstrating Benefits of Enzyme Amplifications in Clinical Chemistry", Clinica Chemica Acta, 148, 119–124, (1985).

Moss, D.W., et al., "An Enzyme–Amplified Monoclonal Immunoenzymometric Assay for Prostatic Acid Phosphatase", Clinica Chimica Acta, 152, 85–94 (1985).

Johannsson, A., et al., "Enzyme Amplification for Immunoassays Detection Limit of One Hundredth of an Attomole", J. Immunological Methods, 87 7–11 (1986).

Stanley, C.J., et al., "Use of a New and Rapid Milk Progesterone Assay to Monitor Reproductive Activity in the Cow", The Veterinarian Record, Jun. 14, 1986, pp. 664–667.

Heap, R.B., et al., "Mechanisms of Transfer of Steroid Hormones and Growth Factors into Milk", Endocrinologia Experimentalis, vol. 20, pp 101–118; 1986.

Worsfold, A.I., et al., "The Evaluation of a New Rapid Milk Progesterone Test as an Aid to Improving Dairy Herd Fertility", British Veterinary Journal, 143, 83–87, 1987.

Stanley, C.J., et al., "Enzyme–Amplified Immunoassays", J. Pharmaceutical and Biomedical Analysis, vol. 5, No. 8, pp. 811–820, 1987.

Stanley, C.J., et al., "Amperometric Enzyme–Amplified Immunoassays", J. Immunological Methods, 112, 153–161, 1988.

Chemical Abstracts 53: 18745 issued 1959, Werdmann et al., "Paper chromatographic separation of copper (II), silver (I), and gold (III)," Osterr. Chemiker Ztg. 60 : 138–139 (1959).

Chemical Abstracts v 5 p. 3753 issued 1911, Fichter et al., "The capillary analyses of colloidal, solutions," Verhandl Naturforsch. Ges. Basel 21 (1910) 1–24.

Chemical Abstracts v 5 p. 3753 issued 1911, Fichter, Z. Chem. Ind. Kolloide, 8 (1911):1–2.

Glad, C. et al.; "Immunocapillarymigration—A new Method for Immunochemical Quantitation", Analytical Biochemistry, 85, 180–187 (1978).

* cited by examiner

TEST DEVICE AND METHOD FOR COLORED PARTICLE IMMUNOASSAY

This is a continuation of application(s) Ser. No. 07/995,331 filed Dec. 23, 1992, now U.S. Pat. No. 5,714,389 which is a File Wrapper Continuation of 07/702,450 filed on May 16, 1991, now abandon which is a File Wrapper Continuation of 07/211,582 filed on Jun. 27,1988.

BACKGROUND OF THE INVENTION

This invention relates to assays for ligands, e.g., antigens, in a liquid sample such as a body fluid. More particularly, the invention relates to a method and apparatus for the detection of a ligand in a body fluid such as urine using a conjugate comprising colored particles and a novel flow-through test cell.

Many types of ligand-receptor assays have been used to detect the presence of various substances, often generally called ligands, in body fluids such as urine. These assays involve antigen antibody reactions, synthetic conjugates comprising radioactive, enzymatic, fluorescent, or visually observable metal sol tags, and specially designed reactor chambers. In all these assays, there is a receptor, e.g., an antibody, which is specific for the selected ligand or antigen, and a means for detecting the presence, and often the amount, of the ligand-receptor reaction product. Most current tests are designed to make a quantitative determination, but in many circumstances all that is required is a positive/negative indication. Examples of such qualitative assays include blood typing and most types of urinalysis. For these tests, visually observable indicia such as the presence of agglutination or a color change are preferred.

Even the positive/negative assays must be very sensitive because of the often small concentration of the ligand of interest in the test fluid. False positives can also be troublesome, particularly with agglutination and other rapid detection methods such as dipstick and color change tests. Because of these problems, sandwich assays and other sensitive detection methods which use metal sols or other types of colored particles have been developed. These techniques have not solved all of the problems encountered in these rapid detection methods.

It is an object of this invention to provide a rapid, sensitive method for detecting ligands in body fluids. Another object is to provide an assay which has high sensitivity and fewer false positives than conventional assays. A further object is to provide a test cell for detection of low levels of ligands in body fluids. Another object is to provide an assay system which involves a minimal number of procedural steps, and yields reliable results even when used by untrained persons.

These and other objects and features of the invention will be apparent from the following description, drawings, and claims.

SUMMARY OF THE INVENTION

The invention features a method and test cell for the detection of a preselected ligand in a liquid sample such as a body fluid.

The test cell useful in the practice of the invention has an elongate outer casing which houses an interior permeable material, e.g., glass fiber, capable of transporting an aqueous solution by capillary action, wicking, or simple wetting. The casing defines a sample inlet, and interior regions which, for ease of description, can be designated as a test volume and a reservoir volume. The reservoir volume is disposed in a section of the test cell spaced apart from the inlet, and preferably is filled with sorbent material. The reservoir acts to receive liquid transported along a flow path defined by the permeable material and extending from the inlet and through the test volume. In the test volume is a test site comprising a first protein having a binding site specific to a first epitope of the ligand immobilized in fluid communication with the flow path, e.g., bound to the permeable material or to latex particles entrapped in or bonded to the permeable material. A window such as a hole or transparent section of the casing permits observations of the test site through the casing wall.

In a preferred embodiment, the flow path is restricted or narrowed in the test area, thereby channeling and concentrating fluid flow into contact with the test site. It is also preferred that the test cell include a solution filtering means disposed in the flow path between the sample inlet and the test site. The filtration means can comprise a separate, conventional filter element disposed within the casing of the test cell in fluid communication with the permeable material defining the flow path, but preferably is defined simply by a portion of the permeable material itself. The provision of such a filtration means in the test cell has the effect of removing by entrapment from impure samples, such as urine samples, a portion of the particulates and nonspecific interfering factors which sometimes cause false positive readings.

The method of the invention requires the use of a conjugate comprising a second protein bound to colored particles such as a metal sol or colloid, preferably gold. The conjugate can take two distinct forms, depending on whether the assay is designed to exploit the "sandwich" or "competitive" technique.

In the case of the sandwich technique, the second protein comprises a site which binds to a second epitope on the ligand. This type of conjugate reacts with the ligand to form a complex in the liquid sample. The complex is detected by visual observation of color development at the test site in the test cell. At the test site, the ligand bound with the conjugate reacts with the immobilized first binding protein to form a "sandwich" of the first protein, ligand, second protein, and colored particles. This sandwich complex is progressively produced at the test site as sample continuously passes by, filling the reservoir. As more and more conjugate is immobilized, the colored particles aggregate at the test site and become visible through the window, indicating the presence of ligand in the liquid sample.

In the case of the competitive technique, the second protein binds with the first protein in competition with the ligand. The second protein comprises, for example, an authentic sample of the ligand or a fraction thereof which has comparable affinity for the first protein. As the liquid sample is transported in contact with the test site, ligand, if any, and the conjugate compete for sites of attachment to the first protein. If no ligand is present, colored particles aggregate at the test site, and the presence of color indicate the absence of detectable levels of ligand in the sample. If ligand is present, the amount of conjugate which binds at the test site is reduced, and no color, or a paler color, develops.

In one embodiment of the invention, the test liquid is mixed with the conjugate outside the test cell. In another embodiment, the conjugate is disposed in freeze-dried or other preserved form on the permeable material between the inlet and the test site, and the sample liquid resolubilizes the conjugate as it passes along the flow path.

Color development at the test site may be compared with the color of one or more standards or internal controls to determine whether the development of color is a true indication of the presence or absence of the ligand, or an artifact caused by nonspecific sorption.

In one embodiment employing the sandwich technique, the standard consists of a negative control site, preferably disposed adjacent the test site, and visible through a second window proximate the first. The negative control site preferably is prepared identically to the test site, except immobilization of the first binding protein is omitted. Therefore, although the conjugate will reach the control site, it aggregates due only to non-specific binding. If the test site is not appreciably more intense in color than the control site, the assay is considered negative.

In another embodiment, the assay and test cell may include a positive control. Thus, when exploiting the sandwich technique, the cell may have an authentic sample of the ligand immobilized at a control site. If no color develops at this control site, the assay is considered inconclusive. When exploiting the competitive technique, the development of color at the positive control site means the assay results are inconclusive.

Broadly, the method of the invention involves the use of a test cell of the type described above to achieve an easily readable, sensitive, reproducible indication of the presence of a ligand, e.g., human chorionic gonadotropin (hCG), in a test sample such as a human urine sample. The method involves the step of transporting the sample and a conjugate comprising a protein bound to a metal sol or other colored particle along a flow path and in contact with a test site comprising immobilized binding protein specific to an epitope of the ligand, and preferably also in contact with a control site. Preferably, the colored particle comprises a gold sol; the flow path in the region of the test site is reduced in cross-section relative to other parts of the flow path; the sample is passed through a filtration means after it enters the test cell but before it contacts the test site; and the test site comprises latex particles entrapped or otherwise fixed in the flow path having the immobilized protein on their surface. In the practice of the process, either the conjugate is premixed with the sample, or the conjugate is disposed in preserved form, e.g., lyophilized, in the flow path between the inlet and the test site. In either case, placement of the test cell in the sample, or application of the sample to the inlet, initiates flow, and the result is read by observing color development as the test site, or by comparing the color of the test site and control site.

The use of the colored particle detection system in combination with the filtration means, the concentrating effect of flow of the sample, and the ease of comparison between the colors of the test and control sites, together enable construction of a family of extremely sensitive assay systems which minimize false positives and can be used effectively by untrained persons.

BRIEF DESCRIPTION OF THE DRAWING

Like reference characters in the respective drawn figures indicate corresponding parts.

DESCRIPTION

Figure 1:
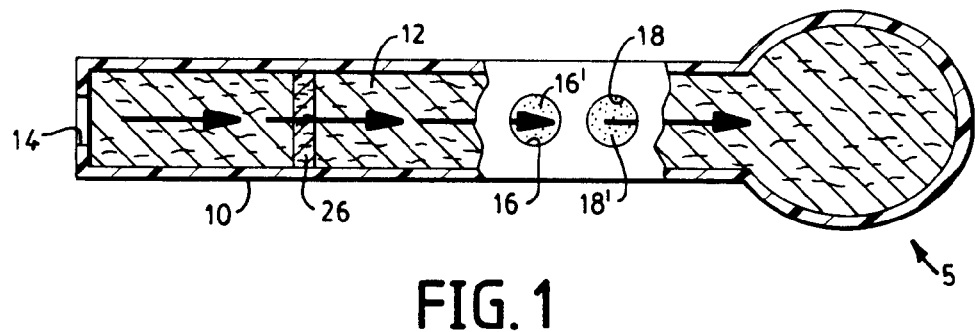
FIG. 1 is a cut-away, schematic, top view of an embodiment of a test cell useful in explaining the test cell and process of the invention.

The invention provides a test cell for conducting a sandwich or competitive immunoassay, and a process which utilizes the test cell and a conjugate comprising colored particles. As disclosed below, various features of the process and test cell of the invention cooperate to enable untrained personnel reliably to assay a liquid sample for the presence of extremely small quantities of a particular ligand while avoiding false positives and simplifying test procedures. The invention is ideal for use in over-the-counter assay test kits which will enable a consumer to self diagnose, for example, pregnancy, venereal disease, and other disease, infection, or clinical abnormality which results in the presence of an antigenic marker substance in a body fluid, including determination of the presence of metabolites of drugs or toxins. The assay process and the cell are engineered specifically to detect the presence of a preselected individual ligand present in a body or other fluids.

Broadly, the test cell and process of the invention can be used to detect any ligand which has heretofore been assayed using known immunoassay procedures, or known to be detectable by such procedures, using polyclonal or monoclonal antibodies or other proteins comprising binding sites for ligands. Various specific assay protocols, reagents, and analytes useful in the practice of the invention are known per se, see, e.g., U.S. Pat No. 4,313,734, columns 4–18, and U.S. Pat. No. 4,366,241, columns 5–40.

The combination of features believed to be responsible for the excellent sensitivity and reproducibility of assays constructed in accordance with the invention is the use of the novel test cell which serves to concentrate ligand from a test sample at a test site in the cell, and the use of a metal sol or other colored particle as a marker system which permits direct visual observation of color development. False positives are reduced while maintaining excellent sensitivity by including in the test cell a negative control or control site whose color is compared with the test site, and by including a filtration means which limits the introduction to the test site of contaminants from the sample.

The assay is conducted by simply placing the inlet of the test cell in contact with a liquid test sample. One then merely waits for the test sample to pass through the cell and into reactive contact with the test site (and optionally one or more control sites) visible through a window or windows in the cell's exterior casing. In one embodiment, the conjugate is mixed with the sample and incubated briefly before the test cell is inserted. In another embodiment, the conjugate is disposed in preserved form in the flow path within the cell. If the ligand is present in the sample, it passes through the inlet and the interior of the cell along the flow path past the test and control sites, where, in the sandwich embodiment, it reacts with immobilized binding protein, e.g., antibody, at the test site, and perhaps also non-specifically at the control site. A "sandwich" forms at the test site comprising immobilized binding protein-ligand binding protein-colored particle. The presence of the sandwich complex and thus the ligand is indicated by the development of color caused by aggregation of the metal sol particles at the test site. A deeper color at the test site than at the negative control site is a positive indication of the presence of the ligand.

By providing a reservoir of sorbent material disposed beyond the test and control sites, a relatively large volume of the test liquid and any ligand it contains can be drawn through the test area to aid sensitivity. Optionally, the region of the flow path in the test cell defining the test and control sites is restricted in cross-sectional area relative to other regions of the flow path. This feature produces a "bottleneck" effect wherein all ligand in the entire volume of sorbed sample must pass through the restricted flow area immediately about the test site where it will be immobilized by reaction with binding protein.

From the foregoing, it will be apparent that the success of the test procedure is dependent on ligand present in the sample reacting with the conjugate, or on reproducible competition between the ligand and the conjugate for sites of attachment at the test site. In accordance with the invention, as noted above, the assays can be conducted by premixing the conjugate with the liquid sample prior to introduction into the elongate test cell. Alternatively, the conjugate may be disposed in preserved form, e.g., freeze-dried, in the flow path within the test cell upstream of the test and control sites. In this case, the cell is placed directly in the liquid sample solution without premixing. Ligand, if any, passing up through the cell and entrained within the liquid moves into contact with the conjugate forming an immune complex or initiating competition in situ as flow continues. This latter technique has the advantage that it eliminates a manipulative step in the assay procedure, and accordingly a possible source of error.

Figure 2:
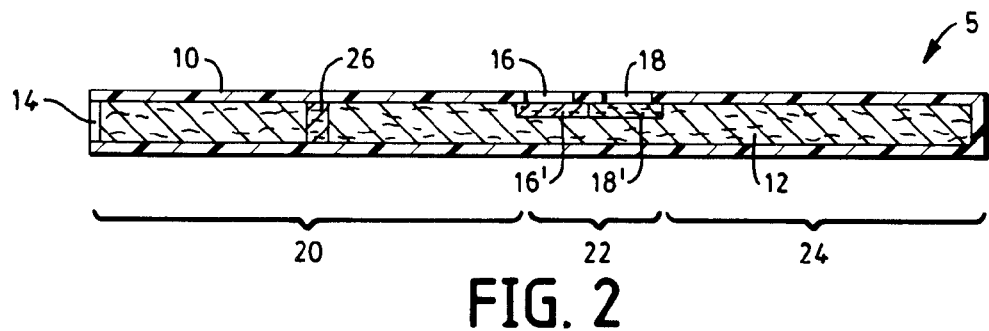
FIG. 2 is a cross-sectional side view of the test cell of FIG. 1.

Referring to the drawing, FIGS. 1 and 2 illustrate schematically an embodiment of a test cell 5 constructed in accordance with the invention useful in explaining its principles of construction. It comprises an outer, molded casing 10 which defines a hollow, elongate enclosure filled with a permeable, sorbent material 12. Casing 10 also defines a test liquid inlet 14 and a pair of circular openings 16, 18 comprising windows through which sorbent material 12 is visible.

Sorbent material 12 and the interior of casing 10 together define a flow path passing generally from left to right in FIGS. 1 and 2. When the test cell is placed with inlet 14 disposed within or otherwise in contact with a liquid sample, the liquid is transported by capillary action, wicking, or simple wetting along the flow path through downstream flow section 20, test volume 22, and into reservoir volume 24, generally as depicted by the arrows. The flow section 20 of the flow path disposed inwardly of the inlet 14 serves as a filter which can remove from impure test samples particulate matter and interfering factors. The provisions of such a filtration means 20 downstream of the inlet 14 is believed to contribute to the success of the system and its ability to avoid false positives.

Disposed within sorbent material 12 is a band 26 of dehydrated conjugate, e.g., antibody-metal sol. As the liquid sample moves past band 26, the conjugate is entrained in the liquid, reconstituted, and reacts or competes with ligand, if present, dissolved in the liquid sample. Of course, conjugate band 26 may be eliminated, and the conjugate added to the test liquid prior to introduction of the cell 5 as previously noted.

Within the volume of sorbent material 12 disposed directly beneath circular openings 16 and 18 in casing 10 is disposed, respectively, control site 16' and test site 18'. In the drawing, the control and test site are illustrated as being disposed serially along the flow path. Alternatively, the control and test site or sites may be disposed side by side or in other spacial relationships.

Test site 18' comprises a preselected quantity of antibody against an epitope of the ligand to be detected immobilized in place within the flow path. Its detailed chemical structure can vary widely. Control site 16' is preferably identical in size and chemical makeup to test site 18', excepting that the immobilized antibody present at the test site 18' is omitted at the control site 16'. Thus, any nonspecific aggregation of, e.g., ligand-conjugate or free conjugate, which occurs at test site 18' also will occur at control site 16'. A deeper color at test site 18' as compared with control site 16' is a positive indication of ligand in the sample in the sandwich assay.

The invention is not limited by the precise nature of the test site 18' and corresponding control site 16', and in fact, control site 16' may be entirely eliminated if a reduction in sensitivity can be tolerated. Generally, antibody or other binding protein may be immobilized at test site 18' using adsorption, absorption, or ionic or covalent coupling, in accordance with methods known per se. A currently preferred formulation for test site 18,' is to immobilize monoclonal antibody against an epitope of the ligand on latex beads, and then to entrap or otherwise link the beads in sorbent material 12 at region 18'. Control site 16' is fabricated identically, except that the latex beads contain non specific immunoglobulin, e.g., immunoglobulin from bleedings from an animal that has not been immunized.

Disposed beyond test volume 22 is a reservoir volume 24 comprising a relatively large mass of sorbent or supersorbent material. The purpose of reservoir volume 24 is to assure that a reasonably large amount of test liquid is drawn through test volume 22. Increasing the volume of reservoir 24 can have the effect of increasing the sensitivity of the assay procedure, as it results in an increase in the amount of ligand passing through the test area 22. Suitable sorbents include commercial materials of the type available, for example, from The Dow Chemical Company of Midland, Mich., and the Chemical division of American Colloid, Arlington Heights, Ill. These materials can absorb many times their weight in water and are commonly used in disposable diapers. They comprise lightly crosslinked polyacrylate salts, typically alkali metal salts.

Polyclonal antisera and indeed monoclonal antibodies or fractions thereof having specific binding properties and high affinity for virtually any antigenic substance are known and commercially available or can be produced from stable cell lines using well known cell fusion and screening techniques. The literature is replete with protein immobilization protocols. See, for example, Laboratory Techniques in Biochemistry and Molecular Biology, Tijssen, Vol. 15, Practice and Theory of Enzyme immunoassays, chapter 13, The Immobilization of Immunoreactants on Solid Phases, pp. 297–328, and the references cited therein.

Metal sols and other types of colored particles useful as marker substances in immunoassay procedures are also known per se. See, for example, U.S. Pat. No. 4,313,734, Feb. 2, 1982, to Leuvering, the disclosure of which is incorporated herein by reference. For details and engineering principles involved in the synthesis of colored particle conjugates see Horisberger, Evaluation of Colloidal Gold as a Cytochromic Marker for Transmission and scanning Electron Microscopy, Biol. Cellulaire, 36, 253–258 (1979); Leuvering et al, Sol Particle Immunoassay, J. Immunoassay 1 (1), 77–91 (1980), and Frens, Controlled Nucleation for the Regulation of the Particle Size in Monodisperse Gold Suspensions, Nature, Physical Science, 241, pp. 20–22 (1973).

The cell can take various forms. It will usually comprise an elongate casing comprising interfitting parts made of polyvinyl chloride, polypropylene, or other thermoplastic resin. Its interior flow path will contain a relatively inert material or a combination of materials suitable for transporting the liquid. In some circumstances it. may be preferable to use a material of higher sorptivity as the reservoir, promoting the flow of liquid, and a different material for remaining portions of the flow path.

From the foregoing it should be apparent that the advantages in reproducibility, sensitivity, and avoidance of false positives of assay systems constructed in accordance with the invention are traceable to a combination of features of the invention. In use, the test cell of the invention and the metal sol particles used as a marker together cooperate to result in an increase in color intensity progressively as ligand completed with conjugate is trapped at the test site by the immobilized binding protein. This approach can be utilized to design assays and test cells for essentially any antigenic material.

The invention will be further understood from the following non-limiting examples.

EXAMPLE 1

Figure 3:
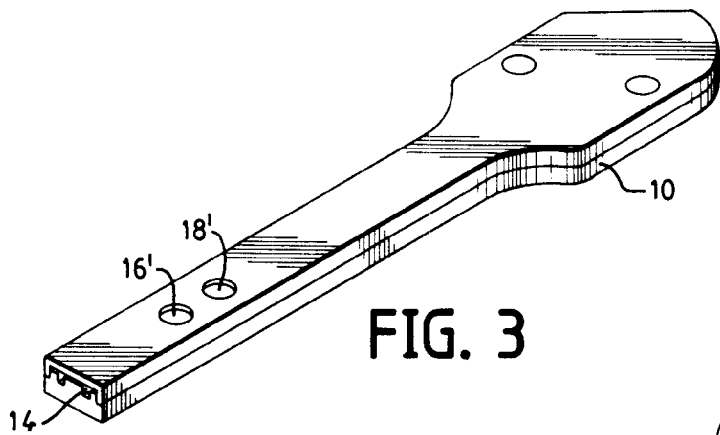
FIG. 3 is a perspective view of a currently preferred test cell constructed in accordance with the invention.
Figure 6:
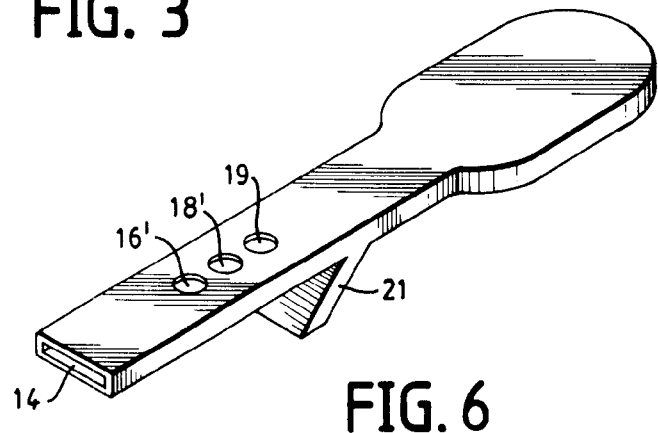
FIG. 6 is a perspective view of another embodiment of a test cell constructed in accordance with the invention.
Figure 4A:
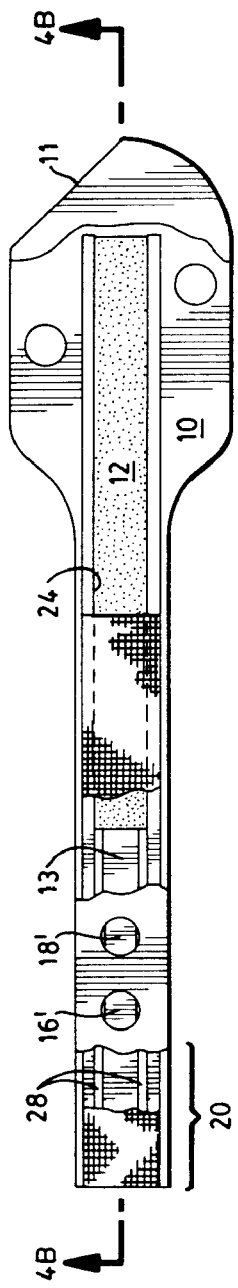
FIG. 4A is a cross-sectional, top view of the test cell of FIG. 3.
Figure 4B:
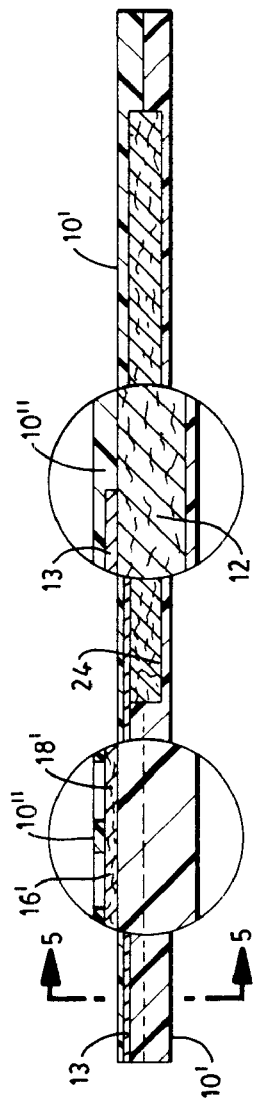
FIG. 4B is a cross-sectional, side view of the test cell of FIG. 3 taken at line 4B—4B of FIG. 4A.

The currently preferred test device embodying the invention is shown in FIGS. 3, 4A, 4B, and 5. A modification of the device depicted in FIG. 3 is shown in FIG. 6, and includes a second control site 19 in addition to control site 16' and test site 18', as well as a stand 21 useful for maintaining the test cell in an incline position with the reservoir downhill. When a test sample is applied to inlet 14, gravity as well as sorption aids in transporting the sample along the flow path.

As shown in FIGS. 3, 4A, 4B, and 5, the preferred test cell of the invention differs from the exemplary device discussed above and shown in FIGS. 1 and 2 in certain of its more specific internal features. Specifically, the casing 10 comprises a pair of interfitting polymeric parts including a U-shaped top part 10' which, when the device is assembled, interfits with lower part 10''. Top and bottom parts 10' and 10'' may be connected through a hinge region 11. The bottom section 10'' defines a pair of channels 28 above which is disposed a strip of glass fiber paper 13 (available commercially from Eaton Dikeman, Grade 111, or Whatman, Grade GFA). Test liquid applied through inlet 14 soaks along the paper strip 13 which defines the flow path and a filtering means region 20, as well as a positive control site 16' and test site 18' visible through windows 16 and 18 consisting of openings through upper mating member 10'. The paper strip 13 overlaps into reservoir volume 24, which is defined by a cavity between the interfitting top and bottom mating members 10' and 10'. The cavity in this case is filled with sorbent blotting paper 12 comprising the sorbent reservoir. A suitable paper is sold as Grade 12 absorbent paper, a cellulose product available from Schleicher and Schuell. In one preferred embodiment, the dimensions of the glass fiber paper 13 were approximately one quarter inch by three inches, and those of the absorbent material 12 approximately two inches by five thirty seconds of an inch on each side. A number of these devices were produced and further treated to adapt them to detect pregnancy by assay of urine.

Test site 18' in each device was fabricated as a spot within fiber paper 13 using the following technique. Latex beads available commercially and comprising polystyrene particles 0.3 micron in diameter were passively coated with purified rabbit anti-human chorionic gonadotropin. The polyclonal, antibody was purified using conventional techniques from bleedings of a rabbit previously immunized with human chorionic gonadotropin in a manner know per se. Equal parts of a latex (0.6% by weight) having a continuous phase of glycine buffer, pH=8.3, and a 1 mg/ml antibody solution in the same buffer were mixed and incubated at 37°C. 15 microliters of this solution, comprising approximately 0.6% solids, were added, one drop at a time, to the glass fiber paper 13 to produce spot 18' after the devices had been assembled. The spots were then allowed to dry at 37° C. The control site 16' was produced identically to the test site disclosed immediately above, excepting that rabbit polyclonal non-immune gamma globulin was used in place of the anti-hCG gamma globulin.

Metal sol particles were prepared in accordance with the method of Frens, Controlled Nucleation for the Regulation of the Particle Size in Mono Dispersed Gold Solutions (1973), supra. Briefly, the gold sol was prepared by reducing a 4% solution of gold chloride with 1% sodium citrate to produce gold particles of approximately 18 nm in diameter. The particles were made immunochemically reactive by admixture with a monoclonal antibody specific for human chorionic gonadotropin with no detectable cross-reactivity with human leutinizing hormone. The antibody was purchased from Charles River Labs, and is produced using standard techniques including purification from ascites using HPLC ion exchange chromatography. It was added to the gold sol as a 10 ug/ml solution in borate buffer, pH-6. The bound antibody fraction is separated from the free fraction by either density centrifugation or gel filtration chromatography. Additional details of the currently preferred procedure for making the antibody sol conjugate are disclosed by Leuvering et al, J. Immunoassay (1980) supra. Individual batches of the latex and the conjugate are titrated to optimize activity so that a suitable amount of latex is applied to the test site and a suitable amount of conjugate is used in conducting the test.

Test Protocol

Figure 5:
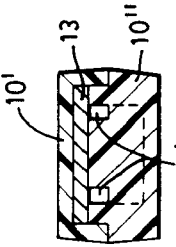
FIG. 5 is a cross sectional view of the cell of FIG. 3 taken at line 5—5 of FIG. 4B.

To a 10×50 mm test tube of lyophilized gold sol antibody conjugate is added 0.5 ml urine sample containing a known quantities of hCG. The samples comprised hCG standards purchased from Sigma Chemical Company diluted in processed, hCG negative urine. The contents of the tube are mixed by shaking in a horizontal motion until the lyophilized antibody is dissolved. The device depicted in FIGS. 3–5 is then inserted into the tube, and the results are read after the entire fluid volume has been absorbed.

The results of this qualitative procedure follows:

| mIU hCG | Color of Control Spot | Color of Reagent Spot |
| --- | --- | --- |
| 0 | grey | grey |
| 25 | grey | pink hue |
| 50 | grey | pink |
| 100 | grey | rose |
| 150 | grey | rose |
| >150 | grey | dark rose |

The pink color clearly visible at 50 mIU of human chorionic gonadotropin means that the test can pregnancy one day after a missed menstrual period. In initial stages of testing, approximately 50 negative samples from various sources have been run with no false positives or even border-line cases. It is anticipated that the commercial device will have less than 1% false positives.

Non-limiting examples of materials which may be assayed in accordance with the invention in addition to the human chorionic gonadotropin noted above include human leutinizing hormone, progesterone, estrogen, and streptoccous.

Other embodiments are within the following claims.

What is claimed is:

1. A test device for determining an analyte in a liquid sample, the device comprising a permeable material defining at least a first portion and a second portion, the portions being in the same plane so as to permit capillary flow communication with each other said first portion being the site for application of the liquid sample, and for a conjugate movably supported therein, wherein said conjugate consists of a binder for the analyte coupled to a colored particle, and said second portion being the site for visually determining the presence of the colored particle, said second portion consisting of a binder immobilized therein which specifically binds to the analyte.

2. A method for determining the presence of an analyte in a liquid sample comprising:

a) adding a liquid sample to a first portion of a test device comprising a permeable material defining at least a first portion and a second portion, the portions being in the same plane so as to permit capillary flow communication with each other said first portion being the site for application of the liquid sample, and for a conjugate movably supported therein, wherein said conjugate consists of a binder for the analyte coupled to a colored particle, and said second portion being the site for visually determining the presence of the colored particle, said second portion consisting of a binder immobilized therein which specifically binds to the analyte;

b) allowing the liquid sample to flow to the second portion of the permeable material; and c) determining the presence of the analyte in the liquid sample by visual inspection of the second portion for color development, wherein the presence of the analyte is indicated by the presence of the colored particles.

3. A test device for detecting an analyte in a liquid sample, the device comprising a permeable material defining at least a first portion and a second portion, the portions being positioned so as to permit capillary flow Communication with each other said first portion being the site for application of the liquid sample, and for a conjugate movably supported therein, wherein said conjugate consists of a binder for the analyte coupled to a colored particle, and said second portion being the site for visually determining the presence of the colored particle, said second portion consisting of a binder immobilized therein which specifically binds to the analyte.

4. A method for determining the presence of an analyte in a liquid sample comprising:

a) adding a liquid sample to a first portion of a test device comprising a permeable material defining at least a first portion and a second portion, the portions being positioned so as to permit capillary flow communication with each other said first portion being the site for application of the liquid sample, and for a conjugate movably supported therein, wherein said conjugate consists of a binder for the analyte coupled to a colored particle, and said second portion being the site for visually determining the presence of the colored particle, said second portion consisting of a binder immobilized therein which specifically binds to the analyte;

b) allowing the liquid sample to flow to the second portion of the permeable material; and c) determining the presence of the analyte in the liquid sample by visual inspection of the second portion for color development, wherein the presence of the analyte is indicated by the presence of the colored particles.

5. A test device comprising a conjugate and a test strip;

the conjugate comprising a first binder for a ligand and a colored particle bound thereto, the conjugate forming a complex with the ligand when present together in liquid;

the test strip comprising a sorbent material defining a flow path extending from a sample application site to at least a test site, the flow path guiding therealong transport of the conjugate and a liquid suspected to contain a ligand;

a second binder for capturing the ligand or the complex, the second binder being immobilized at the test site;

whereby accumulation of colored particles at the test site produces a color visible to the unaided eye indicative of the presence of the ligand in the liquid.

6. The test device of claim 5 wherein the conjugate is disposed in the flow path upstream of the test site and is mobilizable along the flow path with passing liquid.

7. The test device of claim 6 wherein the conjugate is in dry form.

8. The test device of claim 6 wherein the conjugate is transported along the flow path by liquid wicking or wetting through the sorbent material.

9. The test device of claim 5 wherein the second binder comprises an immobilized protein.

10. The test device of claim 5 wherein the second binder comprises an immobilized antibody to the ligand.

11. The test device of claim 5 wherein the first binder comprises a second antibody to the ligand.

12. The test device of claim 5 wherein the first binder binds to human chorionic gonadotropin.

13. The test device of claim 5 wherein the second binder binds to human chorionic gonadotropin.

14. The test device of claim 5 wherein the first binder comprises a monoclonal antibody.

15. The test device of claim 5 wherein the colored particle is a metal sol particle.

16. The test device of claim 15 wherein the metal sol particle is colloidal gold.

17. The test device of claim 5 further comprising a super sorbent material downstream of the test site, the test strip further defining a flow path to the super sorbent material.

18. A method of detecting a ligand in a liquid sample, the method comprising the steps of:

(a) providing a test device comprising a conjugate and a test strip, the conjugate comprising a first binder for a ligand and a colored particle bound thereto, the test strip comprising a sorbent material defining a flow path extending from a sample application site to at least a test site, a second binder for capturing the ligand or the complex, the second binder being immobilized at the test site;

(b) applying a liquid sample to the device upstream of the test site so that the sample and the conjugate are transported to the test site by liquid wicking or wetting along the flow path, and the conjugate forms a complex with the ligand when present together in the liquid; and (c) observing visually the test result at the test site wherein the accumulation of colored particles produces a color indicative of the presence of the ligand in the liquid.

19. The method of claim 18, wherein the conjugate is dried in the flow path upstream of the test site, the liquid sample is applied upstream of the dried conjugate, and the conjugate is mobilized along the flow path by passing liquid.

20. The method of claim 18, comprising the additional step of mixing the conjugate with the liquid sample prior to applying the sample to the test device.

21. The method of claim 20, further comprising the step of allowing liquid to transport the sample and the conjugate to the test site by wicking or wetting along the flow path.

22. An immunoassay method for detecting the presence or concentration of a ligand, the method comprising transporting by wicking or capillary action a liquid suspected to contain the ligand, together with a conjugate comprising a colored particulate material bound to a binder for the ligand, the ligand, or an analog of the ligand, along a flow path to a test site which binds the ligand or a complex of the ligand, thereby to produce a color, visible to the unaided eye, indicative of the presence, absence or concentration of the ligand.

23. A test device comprising a conjugate and a test strip:

the conjugate comprising a ligand or an analog thereof and a colored particle bound thereto;

the test strip comprising a sorbent material defining a flow path extending from a sample application site to at least a test site, the flow path guiding transport therealong of the conjugate and of a liquid suspected to contain a ligand;

a binder for capturing the ligand and the conjugate competitively, the binder being immobilized at the test site;

whereby accumulation of colored particles at the test site produces a color visible to the unaided eye indicative of the absence of a detectable level of the ligand in the liquid.

24. The test device of claim 23 wherein the conjugate is disposed in the flow path upstream of the test site and is mobilizable in the flow path upon passage therealong of liquid.

25. The test device of claim 23 wherein the conjugate is in dry form.

26. The test device of claim 23 wherein the conjugate is transported along the flow path by liquid wicking or wetting through the sorbent material.

27. The test device of claim 23 wherein the colored particle is a metal sol particle.

28. The test device of claim 23 wherein the binder comprises an immobilized antibody to the ligand.

29. The test device of claim 23 wherein the binder comprises a protein.

30. The test device of claim 23 wherein the binder binds to human chorionic gonadotropin.

31. The test device of claim 23 wherein the binder comprises a monoclonal antibody.

32. The test device of claim 23 wherein the conjugate comprises human chorionic gonadotropin or an analog thereof.

33. The test device of claim 23 wherein the conjugate comprises human progesterone or an analog thereof.

34. The test device of claim 23 further comprising a super sorbent material downstream of the test site, the test strip further defining a flow path to the super sorbent material.

35. A method of detecting a ligand in a liquid sample, the method comprising the steps of:

(a) providing a test device comprising a conjugate and a test strip,
the conjugate comprising a ligand or analog thereof and a colored particle bound thereto,
the test strip comprising a sorbent material defining a flow path extending from a sample application site to at least a test site,
a binder for capturing competitively the ligand and the conjugate, the binder being immobilized at the test site;

(b) applying a liquid sample to the device upstream of the test site so that
the sample and the conjugate are transported to the test site by liquid wicking or wetting along the flow path; and (c) observing visually the test result at the test site wherein the accumulation of colored particles produces a color indicative of the absence of a detectable level of the ligand in the liquid.

36. The method of claim 35, wherein the conjugate is dried in the flow path upstream of the test site, the liquid sample is applied upstream of the dried conjugate, and the conjugate is mobilizable along the flow path by passing liquid.

37. The method of claim 35, further comprising the step of mixing the conjugate with the liquid sample prior to applying the sample to the test device.

38. The method of claim 37, further comprising the step of allowing liquid to transport the sample and the conjugate to the test site by wicking or wetting along the flow path.

* * * * *

(12) EX PARTE REEXAMINATION CERTIFICATE (6110th)
United States Patent
Charlton

(10) Number: US 6,485,982 C1
(45) Certificate Issued: *Jan. 29, 2008

(54) TEST DEVICE AND METHOD FOR COLORED PARTICLE IMMUNOASSAY

(75) Inventor: David E. Charlton, Allentown, NJ (US)

(73) Assignee: Church & Dwight Co., Inc., Princeton, NJ (US)

Reexamination Request:
No. 90/007,719, Sep. 15, 2005

Reexamination Certificate for:
Patent No.: 6,485,982
Issued: Nov. 26, 2002
Appl. No.: 08/465,675
Filed: Jun. 6, 1995

(*) Notice: This patent is subject to a terminal disclaimer.

Related U.S. Application Data

(63) Continuation of application No. 07/995,331, filed on Dec. 23, 1992, now Pat. No. 5,714,389, which is a continuation of application No. 07/702,450, filed on May 16, 1991, now abandoned, which is a continuation of application No. 07/211,582, filed on Jun. 27, 1988, now abandoned.

(51) Int. Cl.
*B01L 3/00* (2006.01)
*G01N 33/543* (2006.01)
*G01N 37/00* (2006.01)
*G01N 33/76* (2006.01)
*G01N 33/74* (2006.01)

(52) U.S. Cl. .................. 436/514; 422/55; 422/56; 422/57; 435/176; 435/7.92; 435/970; 427/2.11; 436/169; 436/178; 436/524; 436/525; 436/533; 436/544; 436/810; 436/814; 436/817; 436/818; 436/518; 436/523

(58) Field of Classification Search .............. 436/514, 436/518, 523–525, 530, 544, 169, 178, 810, 436/814, 817, 818, 501, 812, 533, 515; 435/176, 435/7.92–7.95, 970, 287.1, 287.2, 287.9, 435/805, 810; 422/55–58; 427/2
See application file for complete search history.

(56) References Cited

U.S. PATENT DOCUMENTS

| | | | |
|---|---|---|---|
| 3,620,677 A | 11/1971 | Morison | 23/253 |
| 3,811,840 A | 5/1974 | Bauer et al. | 23/253 TP |
| 3,888,629 A | 6/1975 | Bagshawe | 23/230 B |
| 4,042,335 A | 8/1977 | Clement | 23/253 |
| 4,045,384 A | 8/1977 | Dorman | 260/8 |

(Continued)

FOREIGN PATENT DOCUMENTS

| | | |
|---|---|---|
| AU | 51315/85 | 5/1986 |
| AU | A 63502/86 | 10/1986 |

(Continued)

OTHER PUBLICATIONS

Leuvering et al. J. Immunoassay, vol. 1(1) pp. 77–91(1980).*
Collins, "Alternative Assays", (Ed. John Wiley & Sons: 1985) pp. 39–59.*

(Continued)

*Primary Examiner*—Ponnaluri Padmashri

(57) ABSTRACT

Disclosed is a test cell and a method for detection of a preselected ligand in a liquid sample such as a body fluid. The test cell includes an elongate outer casing which houses an interior permeable material capable of transporting an aqueous solution and defining a sample inlet, a test volume, and a reservoir volume. The reservoir volume is disposed in a section of the test cell spaced apart from the inlet and is filled with sorbent material. The reservoir acts to receive liquid transported along a flow path defined by the permeable material and extending from the inlet and through the test volume. In the test volume is a test site which includes a first protein having a binding site specific to a first epitope of the ligand immobilized in fluid communication with the flow path. The test site can be observed through a window of the casing.

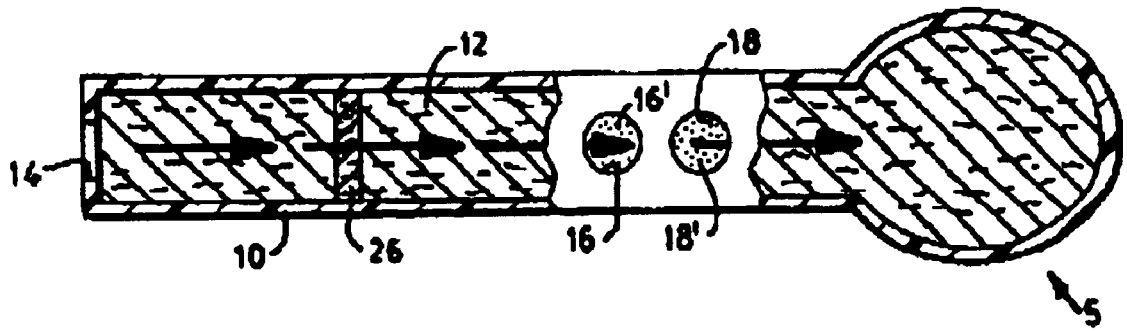

U.S. PATENT DOCUMENTS

| | | | |
|---|---|---|---|
| 4,094,647 A | 6/1978 | Deutsch et al. | 23/253 |
| 4,168,146 A | 9/1979 | Grubb et al. | 23/230 |
| 4,169,138 A | 9/1979 | Jonsson | 424/12 |
| RE30,267 E | 5/1980 | Bruschi | |
| 4,205,952 A | 6/1980 | Cais | 23/230 B |
| 4,219,335 A | 8/1980 | Ebersole | 23/230 B |
| 4,235,601 A * | 11/1980 | Deutsch et al. | 436/514 X |
| 4,256,834 A | 3/1981 | Zuk et al. | 435/7 |
| 4,258,001 A * | 3/1981 | Pierce et al. | |
| 4,266,105 A | 5/1981 | Perkins, Jr. | 422/8 |
| 4,294,818 A | 10/1981 | McMichael et al. | 424/12 |
| 4,297,344 A | 10/1981 | Schwinn et al. | |
| 4,313,734 A | 2/1982 | Leuvering | 23/230 |
| 4,348,207 A | 9/1982 | Cappel | 23/230 B |
| 4,357,142 A | 11/1982 | Schall, Jr. et al. | 23/230 B |
| 4,361,537 A | 11/1982 | Deutsch et al. | 422/56 |
| 4,366,241 A | 12/1982 | Tom et al. | 435/7 |
| 4,373,932 A * | 2/1983 | Gribnau et al. | 436/501 |
| 4,376,110 A | 3/1983 | David et al. | 436/513 |
| 4,411,518 A | 10/1983 | Meserol et al. | 356/39 |
| 4,419,453 A | 12/1983 | Dorman et al. | 436/534 |
| 4,434,150 A | 2/1984 | Azad et al. | 424/1.1 |
| 4,435,504 A * | 3/1984 | Zuk et al. | 436/514 X |
| 4,446,232 A | 5/1984 | Liotta | 435/7 |
| 4,452,901 A | 6/1984 | Gordon et al. | 436/506 |
| 4,459,358 A * | 7/1984 | Berke | 436/170 |
| 4,477,575 A * | 10/1984 | Vogel et al. | 422/56 |
| 4,486,530 A | 12/1984 | David et al. | 435/7 |
| 4,487,839 A | 12/1984 | Kamentsky | 436/518 |
| 4,496,654 A | 1/1985 | Katz et al. | 435/7 |
| 4,503,143 A | 3/1985 | Gerber et al. | 435/7 |
| 4,508,829 A | 4/1985 | Sulitzeanu | 436/510 |
| 4,515,889 A | 5/1985 | Klose et al. | |
| 4,517,288 A | 5/1985 | Giegel et al. | 436/55 |
| 4,537,861 A | 8/1985 | Elings et al. | 436/518 |
| 4,552,839 A | 11/1985 | Gould et al. | 435/7.9 |
| 4,590,169 A | 5/1986 | Cragle et al. | 436/523 |
| 4,594,327 A | 6/1986 | Zuk | 436/514 |
| 4,604,364 A | 8/1986 | Kosak | 436/501 |
| 4,623,461 A * | 11/1986 | Hossom et al. | 210/445 |
| 4,624,929 A | 11/1986 | Ullman | 436/179 |
| 4,632,901 A * | 12/1986 | Valkirs et al. | 435/5 |
| 4,639,242 A | 1/1987 | Babson | 494/37 |
| 4,639,419 A | 1/1987 | Olson et al. | 435/5 |
| 4,647,544 A | 3/1987 | Nicoli et al. | 436/518 |
| 4,654,309 A * | 3/1987 | Milnar et al. | 422/56 |
| 4,654,310 A | 3/1987 | Ly | 436/164 |
| 4,654,322 A * | 3/1987 | Holbein et al. | 502/401 |
| 4,665,034 A | 5/1987 | Chandler | 435/287 |
| 4,666,863 A | 5/1987 | Edwards et al. | |
| 4,677,057 A * | 6/1987 | Curtiss et al. | 435/7.92 |
| 4,690,907 A | 9/1987 | Hibino et al. | 436/514 |
| 4,703,017 A * | 10/1987 | Campbell et al. | 436/501 |
| 4,740,468 A | 4/1988 | Weng et al. | |
| 4,756,828 A | 7/1988 | Litman et al. | 435/7.9 |
| 4,757,004 A | 7/1988 | Houts et al. | 435/7.9 |
| 4,761,381 A * | 8/1988 | Blatt et al. | 436/165 |
| 4,770,853 A * | 9/1988 | Bernstein | 422/58 |
| 4,772,550 A | 9/1988 | Greenquist | 435/7.9 |
| 4,774,192 A | 9/1988 | Terminiello et al. | 436/540 |
| 4,366,241 A | 10/1988 | Tom et al. | 435/7 |
| 4,778,751 A | 10/1988 | El Shami et al. | 435/7.9 |
| 4,803,170 A | 2/1989 | Stanton et al. | 436/518 |
| 4,806,311 A | 2/1989 | Greenquist | 422/56 |
| 4,806,312 A | 2/1989 | Greenquist | 422/56 |
| 4,853,335 A * | 8/1989 | Olsen et al. | 436/527 |
| 4,857,453 A | 8/1989 | Ullman et al. | |
| 4,859,612 A | 8/1989 | Cole et al. | 436/523 |
| 4,861,711 A * | 8/1989 | Friesen et al. | 435/7.92 |
| 4,868,108 A | 9/1989 | Bahar et al. | 435/7.9 |
| 4,879,215 A | 11/1989 | Weng et al. | |
| 4,883,688 A | 11/1989 | Houts et al. | 427/285 |
| 4,891,313 A | 1/1990 | Berger et al. | 436/7 |
| 4,900,663 A | 2/1990 | Wie et al. | 435/7 |
| 4,916,056 A | 4/1990 | Brown, III et al. | |
| 4,920,046 A * | 4/1990 | McFarland et al. | 435/7 |
| 4,945,042 A | 7/1990 | Geiger et al. | 435/7 |
| 4,954,452 A | 9/1990 | Yost et al. | |
| 4,956,302 A | 9/1990 | Gordon et al. | 436/161 |
| 4,959,307 A | 9/1990 | Olson | |
| 4,960,691 A | 10/1990 | Gordon et al. | 435/6 |
| 4,962,023 A | 10/1990 | Todd et al. | 435/7 |
| 4,963,468 A | 10/1990 | Olson | 435/7 |
| 4,981,785 A | 1/1991 | Nayak | 435/7 |
| 4,981,786 A * | 1/1991 | Dafforn et al. | 422/56 |
| 4,985,204 A | 1/1991 | Klose et al. | 422/56 |
| 4,999,285 A | 3/1991 | Stiso | |
| 5,006,474 A * | 4/1991 | Horstman et al. | 422/56 |
| 5,008,080 A * | 4/1991 | Brown, III et al. | 422/56 |
| 5,030,558 A | 7/1991 | Litman et al. | 435/7.91 |
| 5,039,607 A | 8/1991 | Skold et al. | 435/7.5 |
| 5,043,428 A | 8/1991 | Heimburger et al. | |
| 5,073,484 A | 12/1991 | Swanson et al. | 435/7.92 |
| 5,075,078 A | 12/1991 | Osikowicz et al. | 422/56 |
| 5,085,987 A | 2/1992 | Olson | |
| 5,085,988 A | 2/1992 | Olson | |
| 5,120,504 A | 6/1992 | Petro-Roy et al. | 422/58 |
| 5,120,643 A * | 6/1992 | Ching et al. | 435/7.92 |
| 5,141,850 A | 8/1992 | Cole et al. | 436/525 |
| 5,141,875 A | 8/1992 | Kelton et al. | 436/514 |
| 5,149,622 A * | 9/1992 | Brown et al. | 435/5 |
| 5,156,952 A | 10/1992 | Litman et al. | 435/7.91 |
| 5,160,701 A | 11/1992 | Brown, III et al. | |
| 5,164,294 A | 11/1992 | Skold et al. | 435/7.5 |
| 5,232,835 A | 8/1993 | Litman et al. | 435/7.93 |
| 5,248,619 A | 9/1993 | Skold et al. | 436/514 |
| RE34,405 E | 10/1993 | Gould et al. | |
| 5,254,458 A | 10/1993 | Mimms | |
| 5,260,193 A | 11/1993 | Olson | |
| 5,260,194 A | 11/1993 | Olson | |
| 5,266,497 A | 11/1993 | Imai et al. | 436/514 |
| 5,310,650 A | 5/1994 | McMahon et al. | |
| 5,459,078 A | 10/1995 | Kline et al. | |
| 5,459,080 A | 10/1995 | Adamczyk et al. | |
| 5,541,115 A | 7/1996 | Siegel et al. | |
| 5,591,645 A | 1/1997 | Rosenstein | 436/514 |
| 5,602,040 A | 2/1997 | May et al. | |
| 5,622,871 A * | 4/1997 | May et al. | 436/514 |
| 5,654,162 A | 8/1997 | Guire et al. | 435/7.92 |
| 5,656,503 A | 8/1997 | May et al. | 436/514 |
| 5,662,871 A | 9/1997 | Nyman et al. | |
| 5,670,381 A | 9/1997 | Jou et al. | |
| 5,686,315 A | 11/1997 | Pronovost et al. | 436/510 |
| 5,710,005 A * | 1/1998 | Rittenburg | 435/6 |
| 5,714,389 A | 2/1998 | Charlton et al. | |
| 5,716,778 A | 2/1998 | Weng et al. | |
| 5,753,517 A * | 5/1998 | Brooks et al. | 436/514 |
| 5,989,921 A * | 11/1999 | Charlton et al. | 436/501 |
| 6,187,598 B1 * | 2/2001 | May et al. | 436/514 |
| 6,534,320 B2 * | 3/2003 | Ching et al. | 436/514 |

FOREIGN PATENT DOCUMENTS

| | | |
|---|---|---|
| DE | 3044385 | 6/1982 |
| DE | 3432083 | 3/1986 |
| DE | 8 805 565 | 9/1988 |
| EP | 0007654 | 2/1980 |
| EP | 0018561 | 4/1980 |
| EP | 0018561 | 11/1980 |
| EP | 0032270 | 7/1981 |
| EP | 0063810 | 11/1982 |
| EP | 0 063 810 | 11/1982 |

| | | | |
|---|---|---|---|
| EP | 0088636 | | 9/1983 |
| EP | 0140489 | * | 5/1985 |
| EP | 0 183 442 A2 | | 6/1985 |
| EP | 0149168 | * | 7/1985 |
| EP | 0149168 A1 | | 7/1985 |
| EP | 0 149 168 A1 | | 7/1985 |
| EP | 0154749 | * | 9/1985 |
| EP | 0154749 A1 | | 9/1985 |
| EP | 0 158 746 A2 | | 10/1985 |
| EP | 0158746 | | 10/1985 |
| EP | 0164180 | | 12/1985 |
| EP | 0 170 746 A1 | | 2/1986 |
| EP | 0183442 A2 | | 6/1986 |
| EP | 0186799 | | 7/1986 |
| EP | 0 191 640 A2 | | 8/1986 |
| EP | 192 320 | | 8/1986 |
| EP | 0201079 | | 11/1986 |
| EP | 0212603 A2 | | 3/1987 |
| EP | 0 212 603 | | 3/1987 |
| EP | 0 217 403 A2 | | 4/1987 |
| EP | 0 225 054 A1 | | 6/1987 |
| EP | 0 250 137 A2 | | 12/1987 |
| EP | 256 137 | | 12/1987 |
| EP | 0 258 963 | | 3/1988 |
| EP | 0 258 963 A2 | | 3/1988 |
| EP | 0271204 A2 | | 6/1988 |
| EP | 0284232 A1 | | 9/1988 |
| EP | 284 232 | | 9/1988 |
| EP | 0291194 | | 11/1988 |
| EP | 0299428 A2 | | 1/1989 |
| EP | 0306336 | | 3/1989 |
| EP | 0320240 B1 | | 6/1989 |
| EP | 0337082 | | 10/1989 |
| EP | 0349215 | | 1/1990 |
| EP | 0320240 B1 | 3/1991 | ................... 435/6 |
| EP | 0420021 A2 | | 4/1991 |
| EP | 0420021 A2 | | 4/1991 |
| EP | 212599 B1 | | 10/1991 |
| EP | 0505636 A1 | | 9/1992 |
| EP | 0505636 A1 | | 9/1992 |
| EP | 0560410 A2 | | 9/1993 |
| EP | 0560411 | | 9/1993 |
| EP | 0560411 A2 | 9/1993 | ................. 436/518 |
| EP | 0284232 B1 | | 6/1995 |
| FR | 2356944 | | 1/1978 |
| GB | 2 016 687 A | | 9/1979 |
| GB | 2204398 | | 11/1988 |
| JP | 48-49918 | | 7/1973 |
| JP | 53-47894 | | 4/1978 |
| JP | 56-160655 | | 12/1981 |
| JP | 63-25551 | | 11/1984 |
| JP | 61-145459 | | 7/1986 |
| JP | 62-46262 | | 2/1987 |
| JP | 63-32499 | | 2/1988 |
| JP | 1-503174 | | 10/1989 |
| JP | 3125788 | | 1/2001 |
| NL | 8703007 | 12/1983 | ................. 436/525 |
| NL | 8703007 | | 1/1989 |
| WO | WO 86/03839 | | 7/1986 |
| WO | WO 86/04095 | | 7/1986 |
| WO | WO 86/04683 | 8/1986 | ................. 435/7.9 |
| WO | WO 87/02774 | 5/1987 | ................. 435/7.9 |
| WO | WO 88/05912 | | 8/1988 |
| WO | WO88/08534 | | 11/1988 |
| WO | WO 88/08534 | | 11/1988 |
| WO | WO 91/12528 | | 8/1991 |

OTHER PUBLICATIONS

*Grant & Mackh's Chemical Dictionary*, 5th Edition, McGraw–Hill, Inc., 1987, p. 134.*

"*Polar Bear Hits Town; OPUS Immunoassay System*", *Diagnostic News*, issue 1, Mar. 1992, Behring.

"*Summary of Pregslide 00 see Test Specifications*", XII World Congress on Fertility & Sterility, Singapore, 1996.

Baker, T.S., "*Letter to Crawford G.L.: Clarification of Dual Analyte Protocols*". 1983.

Bosch, A.M. G., "*Enzym–und Sol Particle Immunoassays für Hormone*", Gynecology and Obstetrics, p. 509–512; 1987. (English Summary—1 page).

Brdicka, R., "*Grundlagen Der Physikalischen Chemie*", Ch. X, pp. 774–787; Veb Deutscher Verlag Der Wissenschaften, Berlin (1958), (English Summary—1 page).

Bredig–Leipzig, "*Einige Anwendungen Des Elektrischen Lichtbogens*", Zeitschrist Für Electrochemie, Heft. 22, pp. 514–515; (1898). (English Summary—1 page).

Chard, T., "*Pregnancy Tests: A Review*", Human Reproduction, vol. 7, No. 5, pp. 701–710, 1952.

Chemical Abstracts; 5: 3753 (1911); Fichter et al.; "*The capillary analyses of Colloidal Solutions*"; Verhandl Naturforsch. Ges. Basel 21: 1–24 (1910).

Chemical Abstracts; 5: 3753 (1911); Fichter Z.; Chem. Ind. Kolloide, 8: 1–12 (1911).

Chemical Abstracts; 53: 18745 (1959); Werdmann et al.; "*Paper chromatographic separation of Copper (II), Silver (I) and Gold (III)*"; Osterr. Chemiker Ztg. 60: 138–139 (1959).

Collins, H.W.P.; "*Alternative Immunoassays*"; Ed. John Wiley & Sons, 35–58 (1985). (English and Japanese Summary).

Collins, W.P., "*Statutory Declaration No. 2*", In the Matter of European Patent Application No. 88303744.2/291,194, In the Name of Unilever NV and Oppositions Thereto, 1995.

Collins, W.P.; "*Expert Report*"; In the High Court of Justice, Chancery Division, Patent Court; *Unilever PLC v. Chefaro Proprietaries Ltd.*, 1994.

Collins, W.P. *Statutory Declaration*, In the matter of European Patent Application No. 88303744.2–2116 in the name of Unilever, NV, 1992.

*Colloidal Metal Marking Reference Book* (1984–85), vol. 2, No. 1, pp. 1–44.

E. Blasius and M. Fischer, *Papierchromatographische und papierionophoretische Trennung der Platinelemente und des Goldes*, 177 Z. Anal. Chem. (1960), pp. 412–420.

E. Blasius and M. Fischer, *Papierchromatographische und papierionophoretische Trennung der Elemente der Reduktiongruppe*, 178 Z. Anal. Chem. (1960), pp. 28–33.

F. Goppelstroder, Verhandl 3 Naturforsch. Ges. Basel 268 (1861).

Ficher, et al., *Die Kapillaranalyse Kolloidaler Lösungen*, 21 Verhandl Naturforsch.ges.basel 2–24 (1910).

Fichter, *Ueber die kapillarelektrische Fällung positiver Kolloide*, Zeitschrift Für Chemie und Industrie der Kolliode 1–2 (1911).

Frens, "Controlled Nucleation for the Regulation of the Particle Size in Monodisperse Gold Suspensions," 241 Nature Physical Science 20–22 (1973).

Giles, A.B., "*Witness Statement*", In the High Court of Justice, Chancery Division, Patent Court, *Unilever PLC. v. Chefaro Proprietaries Ltd.*; CH 1993. U. No. 3034; 1994.

Glad, C. et al.; "Immunocapillary migration—A New Method for Immunochemical Quantitation"; Analytical Biochemistry, 85, 180–187 (1978).

Greenquist et al.; "*Homogeneous Fluorescent Immunoassay with dry Reagents*"; Clinical Chemistry, 27 (9), 1614–1617 (1981).

Gribnau, et al., *Particle–Labelled Immunoassays: A Review*, 376 J. of Chromatography Biomedical Applications 175–189 (1986).

H. Weil, *Der Ursprung der Papierchromatographie*, 40 Naturwissenschaften (1953), pp. 1–7.

H. Weil, *Der Ursprung der Papierchromatographie*, 40 Naturwissenschaften (1953), pp. 1–7 (see ref. No. 161 for English translation).

H. Weil, *The Evolution of Paper Chromatography*, 132 Kolloid–Z (1953), pp. 149–162.

Heap, R.B., et al., "*Mechanisms of Transfer of Steroid Hormones and Growth Factors into Milk*", Endocrinologia Experimentalis, vol. 20, pp. 101–118; 1986.

Horisberger,"*Evaluation of Colloidal Gold as a Cytochromic Marker for Transmission and Scanning Electron MIcroscopy,*" 36 Biol. Cellulaire 253–58 (1979).

Hornby, W.E., "*Memo; Re: Phase II Threshold Test—Think Tank,*" Unipath, 1986.

Hsu, Y.–H., "Immunogold for Detection of Antigen on Nitrocellulose Paper" Anal. Biochem., 142, 221–225,1984.

J. Perrin, *Mécanisme de L'Electrisation de Contact et Solutions Colloidales*, Tome III J. De Chimie Physique 50–160 (1905).

J. Perrin, *Mécanisme de L'Electrisation de Contact et Solutions Colloidales*, Tome III J. De Chimie Physique 601–51 (1904).

Johannsson, A., et al., "*A Fast Highly Sensitive Colorimetric Enzyme Immunoassay System Demonstrating Benefits of Enzyme Amplifications in Clinical Chemistry*", Clinica Chemica Acta, 148, 119–124, (1985).

Johannsson, A., et al., "*Enzyme Amplification for Immunoassays Detection Limit of One Hundreth of an Attomole*", J. Immunological Methods, 87, 7–11 (1986).

Justice Jacob; "Judgement in *Unilever PLC* v. *Chefaro Proprietaries Ltd.*" In the High Court of Justice, Chancery Division, Ch. 1993 U No. 3034; 1994.

Kronick, M.N., "*Immunoassay Techniques with Fluorescent Phycobiliprotein Conjugates*", Clinical Chemistry, 29/9, 1582–1586, 1983.

Lederer, M., "*Chromatographic Properties of Two Gold Compounds Used in the Therapy of Polyarthritis*", 153 Journal of Chromatography, 302–304 (1978).

Leuvering, et al, "*Sol Particle Immunoassay (SPIA),*" 1 (1) J. Immunoassay 77–91 (1980).

Leuvering, et al., *Optimization of a Sandwich Sol Particle Immunoassay for Human Chorionic Gonadotrophin*, 62 J. of Immunological Methods 175–184 (1983).

Lou, et al., *One–Step Competitive Immunochromatographic Assay for Semiquantitative Determination of Lipoprotein(a) in Plasma*, 39(4) Clin. Chem 619–624 (1993).

Maguire T.A., "*Pregnancy and Ovulation Testing*"; The Pharmaceutical Journal, 531–533, (1989), May 6.

May, K., "*Witness Statement*", In the High Court of Justice, Chancery Division, Patent Court, *Unilever PLC* v. *Chefaro Proprietaries Ltd.*; 1993.

McKelvey, F.E., "*Final Decision*" In the matter of Patent Interference No. 104,148; *David E. Charlton* v. *Robert W. Rosenstein*; 2001.

McKelvey, F.E., "*Final Decision*" In the matter of Patent Interference No. 104,476; *David E. Charlton* v. *Robert W. Rosenstein*; 2001.

Moeremans, M., et al., "*Sensitive Visualization of Antigen–Assays with Immunogold and Immunogold/Silver Staining*", J. Immunological Methods, 74, p. 353–360, 1984.

Moss, D.W. et al., "*An Enzyme–Amplified Monoclonal Immunoenzymometric Assay for Prostatic Acid Phosphatase*", Clinica Chimica Acta, 152, 85–94 (1985).

Puissieux, F et al., "Les Liposomes; Applications Therapeutiques" Technique et Documentation (Lavoisier) 1985, Ch. 2, p. 48 (French, with translation).

Runge, *Die Runft der Farbenbereitung*, FARBENCHEMIE, 1–288, (1850).

Sahlbom, V.N., "*Kapilaranalyse Kolloider Lösungen*", 2 Kolloidchemische Beihefte, Band II, Heft 3–4, pp. 79–140, Verlag Von Theodor Steinkopff, Dresden–A (1910–11).

Stanley, C.J., "*Affidavit*", In the Matter of European Patent No. 291,194 to Unilever, NV and In the Matter of Opposition Thereto, 1994.

Stanley, C.J., "*Witness Statement*", In the High Court of Justice, Chancery Division, Patent Court, *Unilever PLC* v. *Chefaro Proprietaries Ltd.*, 1994.

Stanley, C.J., et al., "*Amperometric Enzyme–Amplified Immunoassays*", J. Immunological Methods, 112, 153–161, 1988.

Stanley, C.J., et al., "*Enzyme Amplification Can Enhance Both the Speed and the Sensitivity of Immunoassays*", J. Immunological Methods, 83, 89–95 (1985).

Stanley, C.J., et al., "*Enzyme Amplification: A New Technique for Enhancing the Speed and Sensitivity of Enzyme Immunoassays*", I.C.P.R., 44–51; Jul./Aug. 1985.

Stanley, C.J., et al., "*Enzyme–Amplified Immunoassays*", J. Pharmaceutical and Biomedical Analysis, vol. 5, No. 8, pp. 811–820, 1987.

Stanley, C.J., "*Use of a New and Rapid Milk Progesterone Assay to Monitor Reproductive Activity in the Cow*", The Veterinarian Record, Jun. 14, 1986, pp. 664–667.

Surek, B. "Visualization of Antigenic Proteins Blotted onto Nitrocellulose Using The Immuno–Gold Staining (IGS) Method" Biochemical and Biophysical Research Communications, 121 (1), 284–289, 1984.

Syva, Syntex Company, Product Brochure "Acculevel; Acculevel TDM Assays", pp. 1–6, Sep. 1987.

Tijssen, Laboratory Techniques in Biochemistry and Molecular Biology, vol. 15, "*Practice and Theory of Enzyme Immunoassays,*" Chapter 13—The Immobilization of Immunoreactants on Solid Phases, 297–328.

Unanue, E.R., Benacerraf, B.; "*Immunfluoreszenz*"; IMMUNOLOGIE, pp. 63–65; Walter de Gruyter, Berlin–New York 1987. (English Translation).

Van Hell, H., et al., "*Particle Immunoassays*"; Alternative Immunoassays, Ch. 4, pp. 40–59; 1985.

Verheijden, P., "*Witness Statement*", In the High Court of Justice, Chancery Division, Patent Court, *Unilever PLC* v. *Chefaro Proprietaries Ltd.*, 1994.

Welch, P.G., "*Witness Statement*", In the High Court of Justice, Chancery Division, Patent Court; *Unilever PLC* v. *Chefaro Proprietaries Ltd.*; 1994.

Wilberg, E., "*Lehrbuch Der Anorganischen Chemie*", pp. 333–338, Walter De Gruyter & Co., Berlin, 1960. (English Summary—1 page).

Worsfold, A.I., et al., "*The Evaluation of a New Rapid Milk Progesterone Test as an Aid to Improving Dairy Herd Fertility*", British Veterinary Journal, 143, 83–87, 1987.

Wright, J.F.; "*A Simple Immunodiagnostics Test System for Alternate Site Market*"; World Biotech Report, pp. 263–271; 1988.

Zsigmondy, R.; "*Ueber Wassrige Lösungen Metallischer Goldes*", Annalen Der Chemie, 301, pp. 29–54; 1898. (German w/ English Translation).

Zuk, R.F., et al., *Enzyme Immunochromatography—A Quantitative Immunoassay Requiring No Instrumentation*, Clinical Chemistry, vol. 31, No. 7, pp. 1144–1150 (1985).

Complaint, dated Aug. 26, 2002.

Defendant's Answer and Counterclaim, dated Nov. 7, 2002.

Reply to Answer and Counterclaim, dated Dec. 2, 2002.

Defendant's Response to Plaintiff's First Set of Interrogatories, dated Apr. 9, 2003.

Quidel's Complaint for Patent Infringement and Declaratory Relief; Demand for Jury Trial, dated Feb. 20, 2004.

Inverness' Complaint; Demand for Jury Trial, dated Mar. 9, 2004.

Answer and Counterclaim of Armkel, LLC; Demand for Jury Trial, dated Mar. 12, 2004.

Second Amended Answer of Inverness Medical Innovations, Inc., Inverness Medical Switzerland GmbH, Applied Biotech, Inc., and Counterclaims of Counter–Plaintiffs; Demand for Jury Trial, dated Apr. 19, 2004.

Inverness' First Amended Complaint; Demand for Jury Trial, dated Apr. 19, 2004.

Quidel Corporation's Answer and Counterclaims; Demand for Jury Trial, dated May 6, 2004.

Claim Construction Brief on Inverness Medical Innovations, Inc., Inverness Medical Switzerland, Applied Biotech, and Wampole Laboratories, dated May 10, 2004.

Declaration of J. Anthony Downs re: Lodgment of Markman Exhibits on Behalf of Claim Construction Brief (with Exhibits L–LL), dated May 10, 2004.

Declaration of Professor Eric J. Toone in Support of Claim Construction Brief of Inverness Medical Innovations, Inc., Inverness Medical Switzerland, Applied Biotech, and Wampole Laboratories, dated May 10, 2004.

Declaration of David F. Katz, Ph. D, in Support of Claim Construction Brief of Inverness Medical Innovations, Inc., Inverness Medical Switzerland, Applied Biotech, and Wampole Laboratories, dated May 7, 2004.

Quidel Corporation's Claim Construction Brief, dated May 10, 2004.

Declaration of Keith A. Orso in Support of Quidel Corporation's Claim Construction Brief, dated May 10, 2004.

Order Construing Disputed Claims of United States No. 6,485,982, dated Jun. 28, 2004.

First Amended Complaint of Inverness, Jun. 6, 2004.

Acon Laboratories' Third Amended Answer and Counterclaim for Declaratory Relief, dated Dec. 23, 2004.

Defendant and Counter–Plaintiff Acon Laboratories' Opposition to Plaintiff's Motion for Preliminary Injunction and Summary Judgment, Sep. 15, 2003.

Affidavit of Dr. Herwig Von Morze in Support of Acon Laboratories' Opposition to Plaintiffs' Motion for Preliminary Injunction and Summary Judgment, Sep. 15, 2003.

Affidavit of David C. Doyle in Support of Acon Laboratories' Opposition to Plaintiffs' Motion for Preliminary Injunction and Summary Judgment, Sep. 15, 2003.

Affidavit of Dr. Gary David in Support of Defendant Acon Laboratories' Opposition to Plaintiffs' Motion for Preliminary Injunction and Summary Judgment, Sep. 15, 2003.

Inverness's Reply Memorandum in Support of Motion for Preliminary Injunction and Summary Judgment of Infringement, Oct. 2, 2003.

Affidavit of Larry S. Nixon in Support of Plaintiffs' Motion for Preliminary Injunction and Summary Judgment, Oct. 3, 2003.

Second Declaration of David F. Katz, Ph.D. in Support of Plaintiffs' Motion for Preliminary Injunction and Summary Judgment, dated Oct. 3, 2003.

Declaration of Michael E. Prior, dated Oct. 3, 2003.

Non–Confidential Declaration of Anastasia Fernands, dated Oct. 3, 2003.

Acon Laboratories' Surreply in Opposition to Inverness's Motion for Preliminary Injunction and Summary Judgment, dated Oct. 17, 2003.

Affidavit of Dr. Gary S. David in Support of Acon Laboratories' Surreply in Opposition to Inverness's Motion for Preliminary Injunction and Summary Judgment, Oct. 17, 2003.

Affidavit of David C. Doyle in Support of Acon Laboratories' Surreply in Opposition to Inverness's Motion for Preliminary Injunction and Summary Judgment, Oct. 17, 2003.

Affidavit of Dr. Herwig Von Morze in Support of Acon Laboratories' Surreply in Opposition to Inverness's Motion for Preliminary Injunction and Summary Judgment, Oct. 17, 2004.

Affidavit of Peng Chen in Support of Acon Laboratories' Surreply in Opposition to Inverness's Motion for Preliminary Injunction and Summary Judgment, Oct. 17, 2004.

Inverness's Further Reply in Support of Motion for Preliminary Injunction and Summary Judgment of Infringement, dated Oct. 28, 2003.

Second Declaration of Michael E. Prior, dated Oct. 28, 2003.

Memorandum in Support of Acon Laboratories' Motion for Summary Adjudication of Invalidity of Claims 5, 6, 7, 18, 19 and 22 of the '982 Patent, dated Nov. 14, 2003.

Acon Laboratories' Local Rule 56.1 Statement of Undisputed Material Facts in Support of Motion for Summary Adjudication of Invalidity of Claims 5, 6, 7, 18, 19 and 22 of the '982 Patent, dated Nov. 14, 2003.

Affidavit of Dr. Gary S. David in Support of Acon Laboratories' Motion for Summary Adjudication of Invalidity of Claims 5, 6, 7, 18, 19 and 22 of the '982 Patent, dated Nov. 14, 2003.

Affidavit of David C. Doyle in Support of Acon Laboratories' Motion for Summary Adjudication of Invalidity of Claims 5, 6, 7, 18, 19 and 22 of the '982 Patent, dated Nov. 14, 2003.

Inverness's and Armkel's Consolidated Opposition to Acon's Motions for Summary Judgment of Invalidity of Claims 5–7, 18–19 and 22, dated Dec. 5, 2003.

Inverness's and Armkel's Consolidated Response to Acon's Local Rule 56.1 Statements of Material Facts in Support of Motions for Summary Judgment of Invalidity of Claims 5–7, 18–19 and 22, Dec. 5, 2003.

Declaration of Eric J. Toone in Support of Inverness's and Armkel's Consolidated Opposition to Acon's Motions for Summary Judgment of Invalidity of Claims 5–7, 18–19 and 22 of the '982 Patent, dated Dec. 5, 2003.

Declaration of David F. Katz, Ph.D. in Support of Inverness's and Armkel's Consolidated Opposition to Acon's Motions for Summary Judgment of Invalidity of Claims 5–7, 18–19 and 22 of the '982 Patent, dated Dec. 5, 2003.

Declaration of Anastasia M. Fernands in Support of Inverness's and Armkel's Consolidated Opposition to Acon's Motions for Summary Judgment of Invalidity of Claims 5–7, 18–19 and 22, dated Dec. 5, 2003.

Declaration of Michael E. Prior, dated Dec. 5, 2003.

Declaration of Margaret M. Mazzeo in Support of Inverness's and Armkel's Consolidated Opposition to Acon's Motions for Summary Judgment of Invalidity of Claims 5–7, 18–19 and 22 of the '982 Patent, dated Dec. 5, 2003.

Declaration of David E. Charlton, dated Dec. 5, 2003.

Acon Laboratories' Reply in Support of Motions for Summary Adjudication of Invalidity of Claims 5, 6, 7, 18, 19 and 22 of the '982 Patent, dated Dec. 15, 2003.

Acon Laboratories' Response to Inverness's and Armkel's Consolidated Response to Acon's Local Rule 56.1 Statement of Material Facts in Support of Motions for Summary Adjudication of Invalidity of Claims 5, 6, 7, 18, 19 and 22 of the '982 Patent, Dec. 15, 2003.

Affidavit of Dr. Gary S. David in Support of Acon Laboratories' Reply Re Motions for Summary Adjudication of Invalidity of Claims 5, 6, 7, 18, 19 and 22 of the '982 Patent (Impounded), dated Dec. 15, 2003.

Affidavit of David C. Doyle in Support of Acon Laboratories' Motions for Summary Adjudication of Invalidity of Claims 5, 6, 7, 18, 19 and 22 of the '982 Patent, dated Dec. 15, 2003.

Inverness's and Armkel's Sur–Reply to Acon's Motions for Summary Judgment of Invalidity of Claims 5–7, 18–19 and 22, dated Dec. 15, 2003.

Declaration of Eric J. Toone in Support of Plaintiffs' Sur–Reply in Opposition to Acon's Invalidity Summary Judgment Motions, dated Dec. 22, 2003.

Fourth Declaration of Michael E. Prior, dated Dec. 22, 2003.

Declaration of Anastasia M. Fernands in Support of Inverness's and Armkel's Sur–Reply to Acon's Motions for Summary Judgment of Claims 5–7, 18–19, and 22, Dec. 22, 2003.

Acon Laboratories' Response to Sur–Reply to Acon's Motions for Summary Judgment or Invalidity of Claims 5, 6, 7, 18, 19 and 22 of the '982 Patent, dated Dec. 30, 2003.

Affidavit of Dr. Gary S. David in Support of Acon Laboratories' Response to Sur–Reply re Motions for Summary Adjudication Invalidity of Claims 5, 6, 7, 18, 19 and 22 of the '982 Patent, dated Dec. 30, 2003.

Order on Invalidity of Claims 5, 6, 18, and 22 of the '982 Patent, dated May 10, 2005.

Memorandum & Order, dated Jul. 16, 2004.

Confidential Memorandum In Support of Motion for Reconsideration of the Court's Jul. 16, 2004 Memorandum and Order re: Invalidity for Failure to Comply with Best Mode and Inequitable Conduct, dated Jul. 27, 2004.

Confidential Affidavit of M. Andrew Woodmansee In Support Acon Laboratories' Motion for Reconsideration of the Court's Jul. 16, 2004 Memorandum and Order Re: Invalidity for Failure to Comply with Best Mode and Inequitable Conduct, dated Jul. 27, 2004.

Plaintiffs' Consolidated Opposition to Acon's Motion for Reconsideration of the Court's Injunction Order, dated Aug. 10, 2004.

Confidential Declaration of Anastasia M. Fernands, dated Aug. 10, 2004.

Declaration of Anastasia M. Fernands, dated Aug. 10, 2004.

Acon Laboratories' Reply in Support of Motion for Reconsideration of the Court's Order re Invalidity for Failure to Comply with Best Mode and Inequitable Conduct, dated Aug. 17, 2004.

Plaintiffs' Surreply in Further Opposition to Acon's Motion for Reconsideration of the Court's Injunction Order, dated Sep. 2, 2004.

Acon Laboratories' Response to Surreply re Motion for Reconsideration of the Court's Order re Invalidity for Failure to Comply with Best Mode and Inequitable Conduct, dated Sep. 7, 2004.

Affidavit of Steven E. Comer In Support Acon Laboratories' Response to Surreply Re: Motion for Reconsideration of the Court's Order re: Invalidity for Failure to Comply with Best Mode and Inequitable Conduct, dated Sep. 7, 2004.

Defendant Acon Laboratories, Inc.'s Trial Brief, dated Nov. 1, 2004.

Plaintiffs' Trial Brief, dated Nov. 1, 2004.

Plaintiffs' Motion Pursuant to Fed. R. Civ. p. 50 for Judgment as a Matter of Law on Anticipation, Best Mode and Obviousness, dated Nov. 19, 2004.

Memorandum of Points and Authorities in Support of Acon Laboratories' Renewed Motion for Judgment As A Matter of Law of Invalidity of Claims 7 and 19 of the '982 Patent As Obvious Under 35 U.S.C. 103, dated Dec. 6, 2004.

Affidavit of David C. Doyle In Support of Acon Laboratories' Renewed Motion for Judgment As A Matter of Law of Invalidity of Claims 7 and 19 of the '982 Patent As Obvious Under 35 U.S.C. 103, dated Dec. 6, 2004.

Plaintiffs' Opposition to Acon Laboratories' Renewed Motion For Judgment As Matter of Invalidity, dated Dec. 21, 2004.

Declaration of J. Anthony Downs, Esq. In Support of Plaintiffs' Opposition to Acon Laboratories' Renewed Motion For Judgment As Matter of Law of Invalidity, attaching Exhibits A–L, dated Dec. 21, 2004.

Reply In Support of Acon Laboratories' Renewed Motion for Judgment As A Matter of Law of Invalidity of Claims 7 and 19 of The '982 Patent As Obvious Under 35 U.S.C. 103, dated Jan. 5, 2005.

Affidavit of David C. Doyle In Support of Acon Laboratories' Reply In Support of It's Renewed Motion For Judgment As A Matter of Law of Invalidity of Claims 7 and 19 of the '982 Patent As Obvious Under 35 U.S.C. 103, dated Jan. 5, 2005.

Plaintiffs' Sur–Reply In Further Opposition To Acon Laboratories' Motion For Judgment as a Matter of Law of Invalidity, dated Jan. 21, 2005.

Acon's Restatement of Motion for Summary Adjudication of Invalidity of Claims 5, 6, 18, and 22 of the '982 Patent, dated Feb. 2, 2005.

Plaintiffs' Opposition to Acon's Restatement of Motion for Summary Adjudication of Invalidity of Claims 5, 6, 18, and 22 of the '982 Patent, dated Feb. 16, 2005.

Acon's Reply in Support of Restatement of Motion for Summary Adjudication of Invalidity of Claims 5, 6, 18, and 22 of the '982 Patent, dated Feb. 2, 2005.

Plaintiffs' Local Rule 56.1 Statement In Support of Motion for Partial Summary Judgment of Validity on the Basis of Written Description (No. 1), dated Dec. 2, 2005.

Declaration of Anastasia M. Fernands In Support of Plaintiffs' Motion for Partial Summary Judgment Against Acon's Written Description Theory (No. 1), dated Feb. 2, 2005.

Plaintiffs' Memorandum In Support of Their Motion for Partial Summary Judgment Against Acon's Written Description Theory (No. 1), dated Feb. 2, 2005.

Confidential Declaration of Anastasia M. Fernands in Support of Plaintiffs' Motion for Partial Summary Judgment Against Acon's Written Description Theory (No. 1), dated Feb. 2, 2005.

Acon Laboratoties, Inc.'s Opposition to Plaintiffs' Motion for Plaintiff's Motion for Partial Summary Judgment of Validity on the Basis of Written Description (No. 1), dated Feb. 6, 2005.

Acon Laboratoties, Inc.'s Response to Plaintiffs' Local Rule 56.1 Statement Re Motion for Partial Summary Judgment Of Validity On the Basis of Written Description (No. 1), dated Feb. 16, 2005.

Affidavit of Brian M. Kramer In Support of Acon Laboratoties, Inc.'s Opposition to Plaintiffs' Motion for Partial Summary Judgment Of Validity on the Basis of Written Description (No. 1), dated Feb. 16, 2005.

Affidavit of Randolph Wall, Ph.D. In Support of Acon Laboratories, Inc.'s Opposition to Plaintiffs' Motion for Partial Summary Judgment of Validity of the Basis Of Written Description (No. 1), dated Feb. 15, 2005.

Plaintiffs' Reply Brief In Support of Their Motion For Partial Summary Judgment Against Acon's Written Description Theory (No. 1), dated Feb. 23, 2005.

Declaration of Lana S. Shiferman In Support of Plaintiffs' Reply Brief In Support of Their Motion For Partial Summary Judgment Against Acon's Written Description Theory (No. 1), dated Feb. 23, 2005.

Acon Laboratories, Inc.'s Sur–Reply to Plaintiffs' Motion for Partial Summary Judgment of Validity on the Basis of Written Description (No. 1), dated Mar. 2, 2005.

Affidavit of Brian M. Kramer In Support of Acon Laboratories, Inc.'s Sur–Reply to Motion for Partial Summary Judgment Against Acon's Written Description Theory (No. 1), dated Mar. 2, 2005.

Memorandum and Order, dated Apr. 29, 2005.

Plaintiffs' Memorandum In Support of Motion for Partial Summary Judgment Against Acon's Abandonment Theory (No. 2), dated Feb. 2, 2005.

Plaintiffs' Local Rule 56.1 Statement In Support of Motion For Partial Summary Judgment Against Acon's Abandonment Theory (No. 2), dated Feb. 2, 2005.

Declaration of J. Anthony Downs In Support of Plaintiffs' Motion For Summary Judgment Against Acon's Abandonment Defense (No. 2), dated Feb. 2, 2005.

Acon Laboratories' Opposition to Plaintiffs' Motion for Partial Summary Judgment Regarding Acon's Abandonment Theory (No. 2), dated Feb. 16, 2005.

Acon Laboratories, Inc.'s Response to Plaintiffs' Local Rule 56.1 Statement In Support of Motion for Partial Summary Judgment Against Acon's Abandonment Theory (No. 2), dated Feb. 16, 2005.

Affidavit of Brian M. Kramer In Support of Defendant Acon Laboratories, Inc.'s Opposition to Plaintiffs' Motion for Partial Summary Judgment Regarding Acon's Abandonment Defense (No. 2), dated Feb. 16, 2005.

Plaintiffs' Reply In Support of Their Motion for Partial Summary Judgment Against Acon's Abandonement Theory, dated Feb. 23, 2005.

Declaration of Lana S. Shiferman In Support of Plaintiffs' Motion for Summary Judgment Against Acon's Abandonement Theory, dated Feb. 23, 2005.

Acon Laboratories' Sur–Reply to Motion For Partial Summary Judgment Against Acon's Abandonment Theory (No. 2), dated Mar. 2, 2005.

Affidavit of Brian M. Kramer In Support of Acon Laboratories, Inc.'s Sur–Reply to Motion for Partial Summary Judgment Against Acon's Abandonement Theory (No. 2), dated Mar. 2, 2005.

Memorandum and Order Re: Partial Summary Judgment On Acon's Claim of Invalidity Based on Abandonment, dated Mar. 28, 2005.

Acon's Laboratories' Confidential Memorandum In Support of Motion For Reconsideration and To Vacate the Court's Memorandum and Order Re: Partial Summary Judgment On Acon's Claim of Invalidity Based On Abandonement, dated Apr. 11, 2005.

Confidential Affidavit of David C. Doyle In Support of Acon Laboratories' Motion For Reconsideration and To Vacate the Court's Memorandum and Order Re: Abandonment, dated Apr. 11, 2005.

Plaintiffs' Memorandum In Support for Partial Summary Judgment on Acon's Inventorship Theory of Inequitable Conduct (No. 3), dated Feb. 2, 2005.

Plaintiffs' Local Rule 56.1 Statement In Support of Motion for Summary Judgment on Acon's Inventorship Theory of Inequitable Conduct (No. 3), dated Feb. 2, 2005.

Declaration of Anastasia M. Fernands In Support of Plaintiffs' Motion For Partial Summary Judgment on Acon's Inventorship Theory of Inequitable Conduct (No. 3), dated Feb. 2, 2005.

Acon Laboratories, Inc.'s Opposition to Plaintiffs' Motion for Partial Summary Judgment on Acon's Inventorship Theory of Inequitable Conduct (No. 3), dated Feb. 16, 2005.

Confidential Affidavit of Brian M. Kramer In Support of Acon Laboratories, Inc.'s Response to Plaintiffs' Local Rule 56.1 Statement RE Motion for Partial Summary Judgment on Acon's Inventorship Theory of Inequitable Conduct (No. 3), dated Feb. 16, 2005.

Non–Confidential Affidavit of Brian M. Kramer In Support of Acon Laboratories, Inc.'s Opposition To Motion For Partial Summary Judgment On Acon's Inventorship Theory of Inequitable Conduct (No. 3), dated Feb. 16, 2005.

Plaintiffs' Reply In Support of Motion For Partial Summary Judgment On Acon's Inventorship Theory Of Inequitable Conduct (No. 3), dated Feb. 23, 2005.

Declaration of Lana S. Shiferman In Support of Motion For Summary Judgment On Acon's Inventorship Theory of Inequitable Conduct, dated Feb. 23, 2005.

Acon Laboratories' Sur–Reply To Motion For Partial Summary Judgment On Acon's Inventorship Theory of Inequitable Conduct (No. 3), dated Mar. 2, 2005.

Affidavit of M. Andrew Woodmansee In Support of Acon Laboratories, Inc.'s Sur–Reply to Plaintiffs' Motion For Summary Judgment On Acon's Inventorship Theory Of Inequitable Conduct (No. 3), dated Mar. 2, 2005.

Confidential Affidavit of Brian M. Kramer In Support of Acon Laboratories, Inc.'s Sur–Reply To Motion For Summary Judgment On Acon's Inventorship Theory of Inequitable Conduct (No. 3), dated Mar. 2, 2005.

Non–Confidential Affidavit of Brian M. Kramer In Support of Acon Laboratories, Inc.'s Sur–Reply to Motion for Partial Summary Judgment ON Acon's Inventorship Theory Of Inequitable Conduct (No. 3), dated Mar. 2, 2005.

Notice of Electronic Filing—Docket Text: Electronic ORDER entered denying Motion for Partial Summary Judgment in Acon's Inventorship Theory of Inequitable Conduct (No. 3), dated May 9, 2005.
Plaintiffs' Memorandum In Support of Motion for Summary Judgment On Acon's Theory of Inequitable Conduct Based on a 1998 Revocation Decision by the European Patent Office, dated Feb. 2, 2005.
Plaintiffs' Local Rule 56.1 Statement In Support of Motion For Summary Judgment on Acon's Theory of Inequitable Conduct Based on a 1998 Revocation Decision By the European Patent Office (No. 4), dated Feb. 2, 2005.
Declaration of J. Anthony Downs In Support of Plaintiffs' Motion for Summary Judgment on Acon's Theory of Inequitable Conduct Based on a 1998 Revocation Decision by the European Patent Office (No. 4), dated Feb. 2, 2005.
Acon Laboratories' Opposition to Plaintiffs' Motion For Partial Judgment Regarding Acon's Inequitable Conduct Defense Regarding The EPO Revocation of The Charlton European Counterpart (No. 4), dated Feb. 16, 2005.
Acon Laboratories, Inc.'s Response to Plaintiffs' Local Rule 56.1 Statement In Support of Motion For Summary Judgment On Acon's Theory of Inequitable Conduct Based On A 1998 Revocation Decision By the European Patent Office (No. 4), dated Feb. 16, 2005.
Affidavit of Steven E. Comer In Support of Acon Laboratories' Opposition To Plaintiffs' Motion for Partial Summary Judgment Regarding Acon's Inequitable Conduct Defense Regarding the EPO Revocation of The Charlton European Counterpart (No. 4), with Exhibits 1–2, dated Feb. 16, 2005.
Affidavit of Dr. Herwig Von Morze, Ph.D., In Support of Acon Laboratories' Opposition to Plaintiffs' Motion for Summary Judgment on Acon's Theory of Inequitable Conduct Based on 1998 Revocation Decision By the European Patent Office, dated Feb. 16, 2005.
Plaintiffs' Reply Brief In Support of Motion for Summary Judgment On Acon's Theory of Inequitable Conduct Based On A 1998 Revocation Decision By the European Patent Office (No. 4), dated Feb. 23, 2005.
Declaration of Lana S. Shiferman In Support of Plaintiffs' Reply Brief In Support of Motion for Summary Judgment On Acon's Theory Of Inequitable Conduct Based On A 1998 Revocation Decision By the European Patent Office, dated Feb. 23, 2005.
Acon Laboratories' Sur–Reply In Opposition to Plaintiffs' Motion For Partial Summary Judgment Regarding Acon's Inequitable Conduct Defense Regarding the EPO Revocation of the Charlton European Counterpart (No. 4), dated Mar. 2, 2005.
Declaration of Joan M. Griffin In Support of Defendant's Sur–Reply In Opposition to Plaintiffs' Motion For Summary Judgment On Acon's Theory of Inequitable Conduct Based On A 1998 Revocation Decision By the European Patent Office (No. 4), dated Mar. 2, 2005.
Notice of Electronic Filing—Docket Text: Electronic ORDER entered denying Motion for Partial Summary Judgment in Acon's Theory of Inequitable Conduct Based on a 1998 Revocation Decision By the European Patent Office (No. 4), dated May 9, 2005.
Acon Laboratories' Pretrial Proposed Findings of Fact and Conclusions of Law, dated Aug. 12, 2005.
Plaintiffs' Trial Brief for the Aug. 15, 2005 Bench Trial on Acon's European Patent Office Revocation Decision Inequitable Conduct Defense, dated Aug. 15, 2005.
Acon Laboratories' Post–Trial Brief, dated Sep. 8, 2005.
Plaintiff's Post–Trial Brief on Acon's European Patent Office Revocation Decision Inequitable Conduct Defense, dated Sep. 8, 2005.
Memorandum in Support of Acon's Motion for Summary Judgment of Non–Infringement and Invalidity of the '389 and '921 Patents, dated May 6, 2005.
Acon's Local Rule 56.1 Statement of Undisputed Material Facts in Support of Motion for Summary Judgment of Non–Infringement and Invalidity of the '389 and '921 Patents, dated May 6, 2005.
Affidavit of Randolph Wall, Ph.D, in Support of Acon's Motion for Summary Judgment of Non–Infringement and Invalidity of the '389 and '921 Patents, dated May 6, 2005.
Plaintiffs' Emergency Motion for Continuance of Their Opposition to Acon's Motion for Summary Judgment Concerning the Charlton '389 and '921 Patents, dated May 16, 2005.
Declaration of J. Anthony Downs Pursuant to Rule 56(f) of the Federal Rules of Civil Procedure, dated May 16, 2005.
Plaintiff's Opposition to Acon's Motion for Summary Judgment Concerning the Charlton '389 and '921 Patents, dated Jul. 19, 2005.
Inverness' Response to Acon's Local Rule 56.1 Statement of Undisputed Material Facts in Support of Acon's Motion for Partial Summary Judgment of Non–Infringement and Invalidity of the '389 and '921 Patents, dated Jul. 19, 2005.
Declaration of David F. Katz, Ph.D. in Support of Plaintiffs' Opposition to Acon's Motion for Summary Judgment Concerning the '389 and '921 Patents, dated Jul. 19, 2005.
Non–Confidential Declaration of J. Anthony Downs, Esq., in Support of Plaintiffs' Opposition to Acon's Motion for Summary Judgment Concerning the Charlton '389 and '921 Patents, dated Jul. 19, 2005.
Declaration of Michael E. Prior, dated Jul. 19, 2005.
Reply Brief in Support of Acon's Motion for Summary Judgment of Non–Infringement and Invalidity of the '389 and '921 Patents, dated Aug. 12, 2005.
Further Affidavit of Steven E. Comer in Support of Acon's Motion for Summary Judgment of Non–Infringement and Invalidity of the '389 and '921 Patents, dated Aug. 12, 2005.
Confidential Report of Gary S. David on the Invalidity Issues of the Asserted Claims of the Charlton Patents, dated Jun. 21, 2004.
Expert Report of Dr. Herwig Von Morze, dated Jun. 21, 2004.
Confidential Supplemental Report of Gary S. David on the Invalidity Issues to Charlton Patents 5,714,389 and 5,989,921 to Charlton et al, dated Jul. 30, 2004.
Second Confidential Supplemental Report of Gary S. David on the Invalidity Issues to Charlton Patents 5,714,389, 5,989,921 and 6,485,982 to Charlton et al, dated Aug. 26, 2004.
Third Confidential Supplemental Report of Gary S. David on the Invalidity Issues to Charlton Patents 5,714,389, 5,989,921 and 6,485,982 to Charlton et a, dated Sep. 7, 2004.
Affidavit of Dr. Dr. Jinn–Nan Lin, dated Sep. 7, 2004.
Report of Randolph Wall, Ph.D. on the Invalidity Issues of U.S. Patent 6,485,982, dated Jan. 21, 2005.
Expert Witness Report of Larry S. Nixon Pursuant to Fed. R. Civ. P. Rule 26(a)(2)(B), dated Jul. 22, 2004.

Expert Witness Report of Gene A. Davis, Ph.D. on Validity Issues Concerning the Asserted Claims of the Charlton Patents, dated Jul. 28, 2004.
Expert Report of Michael E. Prior Concerning the Validity of the '982 Patent, dated Jul. 30, 2004.
Expert Report of David F. Katz, Ph.D. on Validity Issues Concerning the Charlton Patents, dated Jul. 30, 2004.
Expert Report of Professor Eric J. Toone on Validity Issues, dated Jul. 30, 2004.
Expert Witness Report of Scott A. Chambers, Ph.D., dated Sep. 10, 2004.
Supplemental Expert Report of Professor Eric J. Toone on Validity Issues (Enablement), dated Mar. 11, 2005.
Supplemental Expert Witness Report of Larry S. Nixon Pursuant to Fed. R. Civ. P. Rule 26(a)(2)(B), dated May 12, 2005.
Complaint, dated Apr. 20, 2005.
Answer to Complaint with Jury Demand and Counterclaim, dated Sep. 6, 2005.
Opposition Brief of Andrea von Preen—Request for Revocation, dated Jan. 8, 1996 (and English Translation).
Center Wallace's Observations in Reply to Opposition Brief, dated Aug. 15, 1996.
Rebuttal of Opposer, dated Apr. 8, 1997 (and English Translation).
Preliminary Decisions Revoking the European Patent, dated Jan. 28, 1998.
Submission by Opposer, dated Jul. 27, 1998 (and English Translation).
Final Decision Revoking the Charlton's European Patent, dated Nov. 24 ,1998.
Notice of Reason for Revocation, dated Dec. 14, 2001 (and English Translation).
Opposition Brief of Yoko Kamisaka, dated Jul. 23, 2001 (and English Translation).
Opposition Brief of Abbott Laboratories, dated Jul. 23, 2001 (and English Translation).
Defendant–Appellant Acon's Brief, dated Apr. 18, 2005.
Plaintiff–Appellees' Brief, dated May 31, 2005.
Defendant–Appellant Acon's Reply Brief, dated Jun. 24, 2005.
Final Decision in Interference 104,148, dated Apr. 2, 2001.
Decision on Arbitration Pursuant to 37 CFR 1.690 in the '148 Interference, dated Feb. 8, 2001.
Memorandum Opinion and Order (Decision on Preliminary and Other Motions), dated Mar. 8, 2000.
Amendment ('675 application), dated Mar. 13, 2000.
Order Redeclaring Interference, dated Mar. 15, 2000.
Supplemental Amendment and Remarks ('675 application), dated Aug. 24, 2001.
Senior Party Rosenstein's Motion No. 3 (To add Charlton's Patent To the Interference), dated Feb. 5, 1999.
Charlton's Opposition 3 (to Motion to Add Charlton's Patent to the Interference), dated Feb. 19, 1999.
Senior Party Rosenstein's Reply No. 3 (In Support of Motion to Add Charlton's Patent), dated Feb. 26, 1999.
Order Denying Motion to Add Charlton Patent, dated Mar. 30, 1999.
Memorandum Opinion in Support of Order Denying Motion to Add Charlton Patent, dated Apr. 6, 1999.
Information Disclosure Statement ('582 application), mailed on Aug. 22, 1988, considered by the examiner on Sep. 17, 1991.
Supplemental Information Disclosure Statement ('582 application), mailed on Dec. 2, 1991, considered by the examiner on Mar. 5, 1992.
Information Disclosure Statement ('675 application), dated Feb. 2, 1996, considered by the Examiner Spiegel on Sep. 23, 1996.
Supplemental Information Disclosure Statement ('450 application), dated Dec. 1, 1992, considered May 19, 1993.
Office Action ('450 application), dated Dec. 22, 1992.
Supplemental Information Disclosure Statement ('450 application), dated May 13, 1992, considered by the examiner on Oct. 11, 1994.
Supplemental Information Disclosure Statement ('331 application), dated Apr. 12, 1995, reviewed by the Examiner Spiegel on Jul. 5, 1995.
Information Disclosure Statement ('331 application), dated Feb. 1, 1996.
Supplemental Information Disclosure Statement ('675 application), dated Apr. 12, 1996, considered by the Examiner Spiegel on Sep. 24, 1996.
Amendment and Response After Final ('331 application), dated Mar. 3, 1997.
Office Action ('331 application), dated Jun. 8, 1993.
Interview Summary by Examiner Pyon ('331 application), dated Oct. 26, 1993.
Response ('331 application), dated Dec. 8, 1993.
Office Action ('331 application), dated Mar. 8, 1994.
Response ('331 application), dated Sep. 8, 1994.
Office Action ('331 application), dated Oct. 12, 1994.
Complaint, dated Mar. 13, 1998.
Answer to Complaint and Counterclaim by Conopco, Inc. against Carter–Wallace, Inc., dated May 1, 1998.
Special Verdict.
Romaco, E. L., et al., "An Antiglobulin Reagent Labelled With Colloidal Gold For Use In Electron Microscopy," IMMUNOCHEMISTRY 1974, vol. 11, pp. 521–522.
Frens, G., "Controlled Nucleation for the Regulation of the Particle Size in Monodisperse Gold Suspension," Nature Physical Science, vol. 241, Jan. 1, 1973.
Hoye, Age, "Determination of Radiochemical Purity of Some Radiochemicals and Pharmaceuticals by Paper Chromatography, Thin–Layer Chromatography and High–Voltage Electrophoresis," Journal of Chromatography, 28 (1967) 379–384.
Acon Laboratories, Inc.'s Response to Plaintiffs' Local Rule 56.1 Statement Re Motion for Partial Summary Judgment on Acon's Inventorship Theory of Inequitabe Conduct (No. 3), dated Feb. 16, 2005.
Affidavit of Henry A. Graham, Jr., Ph.D., In Support of Acon Laboratories' Opposition to Motion For Partial Summary Judgment on Acon's Inventorship Theory of Inequitable Conduct (No. 3), dated Feb. 16, 2005.
Affidavit of Ernest G. Schutt In Support of Acon Laboratories' Opposition to Motion For Partial Summary Judgment On Acon's Inventorship Theory Of Inequitable Conduct (No. 3), dated Feb. 16, 2005.
Supplemental Expert Report of Michael E. Prior Concerning Acon's Inequitable Conduct Theory Based on Alleged Inventorship by Ortho Diagnostics, dated Sep. 30, 2005.

* cited by examiner

US 6,485,982 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–4, 6, 18, 20, 24–25 and 37 are cancelled.

Claims 5, 7–8, 19, 21–23, 35–36 and 38 are determined to be patentable as amended.

Claims 9–17 and 26–34, dependent on an amended claim, are determined to be patentable.

New claims 39–42 are added and determined to be patentable.

5. A test device comprising a conjugate and a test strip;
[the conjugate comprising a first binder for a ligand and a colored particle bound thereto, the conjugate forming a complex with the ligand when present together in liquid;]
the test strip comprising a sorbent material defining a flow path extending from a sample application site to at least a test site, the flow path guiding therealong transport of the conjugate and a liquid suspected to contain a ligand;
*the conjugate comprising a first binder for a ligand and a colored particle bound thereto, wherein the conjugate is dried on the test strip and forms a complex with the ligand when present together in liquid;*
a second binder for capturing the ligand or the complex, the second binder being immobilized at the test site;
whereby accumulation of colored particles at the test site produces a color visible to the unaided eye indicative of the presence of the ligand in the liquid.

7. [The test device fo claim 6] *A test device comprising a conjugate and a test strip;*
*the test strip comprising a sorbent material defining a flow path extending from a sample application site to at least a test site, the flow path guiding therealong transport of the conjugate and a liquid suspected to contain a ligand;*
*the conjugate comprising a first binder for a ligand and a colored particle bound thereto,* wherein the conjugate is *disposed* in dry form *in the flow path upstream of the test site, is mobilizable along the flow path with passing liquid, and forms a complex with the ligand when present together in liquid;*
*a second binder for capturing the ligand or the complex, the second binder being immobilized at the test site;*
*whereby accumulation of colored particles at the test site produces a color visible to the unaided eye indicative of the presence of the ligand in the liquid.*

8. The test device of claim [6] *7* wherein the conjugate is transported along flow path by liquid wicking or wetting through the sorbent material.

19. [The method of claim 18] *A method of detecting a ligand in a liquid sample, the method comprising the steps of:*
(a) *providing a test device comprising a conjugate and a test strip,*
*the test strip comprising a sorbent material defining a flow path extending from a sample application site to at least a test site,*
*the conjugate comprising a first binder for a ligand and a colored particle bound thereto, wherein the conjugate is dried in the flow path upstream of the test site*[, the liquid sample is applied upstream of the dried conjugate, and the conjugate] *and is mobilized along the flow path by passing liquid sample, and*
*a second binder for capturing the ligand or the complex, the second binder being immobilized at the test site;*
(b) *applying a liquid sample to the device upstream of the dried conjugate so that*
*the sample and the conjugate are transported to the test site by liquid wicking or wetting along the flow path, and the conjugate forms a complex with the ligand when present together in the liquid; and*
(c) *observing visually the test result at the test site wherein the accumulation of colored particles produces a color indicative of the presence of the ligand in the liquid.*

21. The method of claim [20] *19*, further comprising the step of allowing liquid to transport the sample and the conjugate to the test site by wicking or wetting along the flow path.

22. An immunoassay method for detecting the presence or concentration of a ligand, the method comprising transporting by wicking or capillary action a liquid suspected to contain the ligand *along a flow path in a test strip to a test site*, together with
a conjugate comprising a colored particulate material bound to a binder for the ligand, the ligand, or an analog of the ligand, *wherein the conjugate at the start of the immunoassay method is in dry form in the flow path upstream of the test site and is mobilizable in the flow path by the liquid*
such that, when the liquid moves along [a] *the* flow path to [a] *the test site, the* test site [which] binds the ligand or a complex of the ligand,
thereby to produce a color *in the test site*, visible to the unaided eye, indicative of the presence, absence or concentration of the ligand.

23. A test device comprising a conjugate and a test strip:
[the conjugate comprising a ligand or an analog thereof and a colored particle bound thereto;]
the test strip comprising a sorbent material defining a flow path extending from a sample application site to at least a test site, the flow path guiding transport therealong of the conjugate and of a liquid suspected to contain a ligand;
*the conjugate comprising a ligand or an analog thereof and a colored particle bound thereto, wherein the conjugate is in dry form in the flow path upstream of the test site and is mobilizable by the liquid;*
a binder for capturing the ligand and the conjugate competitively, the binder being immobilized at the test site;
whereby accumulation of colored particles at the test site produces a color visible to the unaided eye indicative of the absence of a detectable level of the ligand in the liquid.

35. A method of detecting a ligand in a liquid sample, the method comprising the steps of:

(a) providing a test device comprising a conjugate and a test strip,

[the conjugate comprising a ligand or analog thereof and a colored particle bound thereto,]

the test strip comprising a sorbent material defining a flow path extending from a sample application site to at least a test site,

*the conjugate comprising a ligand or analog thereof and a colored particle bound thereto, wherein the conjugate is disposed in dried form in the flow path upstream of the test site and is mobilizable by the liquid sample,* a binder for capturing competitively the ligand and the conjugate, the binder being immobilized at the test site;

(b) applying a liquid sample to the device upstream of the test site so that the sample and the conjugate are transported to the test site by liquid wicking or wetting along the flow path; and (c) observing visually the test result at the test site wherein the accumulation of colored particles produces a color indicative of the absence of a detectable level of the ligand in the liquid.

36. The method of claim 35, wherein the [conjugate is dried in the flow path upstream of the test site, the] liquid sample is applied upstream of the dried conjugate, and the conjugate is mobilizable along the flow path by passing liquid.

38. The method of claim [37] *35*, further comprising the step of allowing liquid to transport the sample and the conjugate to the test site by wicking or wetting along the flow path.

*39. The test device of claim 5, 7 or 23 wherein the test strip comprises one or more portions that define the flow path.*

*40. The test device of claim 39 wherein the test device receives the liquid suspected to contain a ligand on the test strip upstream of the dried conjugate.*

*41. The method of claim 18, 22, or 35 wherein the test strip comprises one or more portions that define the flow path.*

*42. The method of claim 41 wherein the liquid is applied to a portion of the test strip upstream of the dried conjugate.*

\* \* \* \* \*